United States Patent [19]

Shogaki et al.

[11] Patent Number: 5,457,099
[45] Date of Patent: Oct. 10, 1995

[54] CARBOSTYRIL DERIVATIVES AND ANTIALLERGIC AGENT

[75] Inventors: Takeshi Shogaki, Suita; Hiromu Toyoda, Osaka; Takao Kakita, Toyonaka; Masumi Furukawa, Izumisano; Seiichi Nakatsugi, Sakai; Emi Masai, Takaishi; Tsuyako Yashima, Nara; Ikuo Ueda, Toyonaka, all of Japan

[73] Assignee: Sawai Pharmaceutical Co., Ltd., Osaka, Japan

[21] Appl. No.: 81,021

[22] Filed: Jun. 22, 1993

[30] Foreign Application Priority Data

Jul. 2, 1992 [JP] Japan .................... 4-175411

[51] Int. Cl.⁶ .................... C07D 401/06; A61K 31/47
[52] U.S. Cl. .................... 514/212; 514/218; 514/253; 514/312; 540/575; 540/597; 544/363; 546/157; 546/158
[58] Field of Search .................... 544/363; 546/157, 546/158; 514/253, 312, 212, 218; 540/575, 597

[56] References Cited

U.S. PATENT DOCUMENTS

| 4,200,641 | 4/1980 | Vandenberk et al. | 424/267 |
|---|---|---|---|
| 4,742,057 | 5/1988 | Ueda et al. | 514/235.2 |
| 4,983,607 | 1/1991 | Manoury et al. | 514/253 |

FOREIGN PATENT DOCUMENTS

| 0006506 | 1/1980 | European Pat. Off. |
| 0364327 | 4/1990 | European Pat. Off. |
| 56-49359 | 5/1981 | Japan . |
| 63-146872 | 6/1988 | Japan . |
| 2-264773 | 10/1990 | Japan . |

OTHER PUBLICATIONS

Patent Abstracts of Japan, vol. 15, No. 017 (C–096), Jan. 14, 1991 & JP–A–22 64 773.
Patent Abstracts of Japan, vol. 012, No. 410 (C–540), Oct. 28, 1988 & JP–A–63 146 872.
Patent Abstracts of Japan, vol. 005, No. 111 (C–063), Jul. 18, 1981 & JP–A–56 049 359.
Patent Abstracts of Japan, vol. 012, No. 365 (C–532), Sep. 29, 1988 & JP–A–63 119 467.
Fuchs, et al., "4–(Indolyl–3)–1–(benzimidadolonyalkyl)–piperidines, a Novel Group of Potential Antiallergy Compounds" Drug. Res. 35(1), (1985) pp. 272–276.
Chemical Abstract, Nakao, et al., "Preparation of Pyrimidinylpiperazine Compounds as Antianxiety Agents" 109:170460m (1988).
Chemical Abstract, Otsuka Pharmaceutical Co., Ltd., "Carbostyrils", 95:132953j (1981).
Chemical Abstract, Sasaki, et al., "Benzoylpiperidine Derivatives and their Salts as Serotonin Receptor Antagonists" 114:143162n (1990).
Tafusa et al, Chem. Abstract 111:23403h (1989).

*Primary Examiner*—Philip I. Datlow
*Attorney, Agent, or Firm*—Scully, Scott, Murphy & Presser

[57] ABSTRACT

1. A compound of the formula:

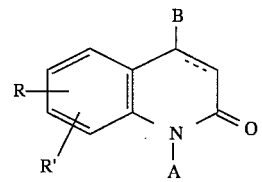

wherein the symbol of a solid line with a broken line means a single bond or a double bond, R and R' are independently selected from the group consisting of hydrogen atom, halogen atom, lower alkyl, nitro, unsubstituted amino and substituted amino, A and B are independently selected from the group consisting of hydrogen atom, lower alkyl optionally substituted with a lower cycloalkyl, aryl optionally substituted with one or more halogen atoms and the group: $-Y-R^2$ wherein Y is lower alkylene and $R^2$ is the group:

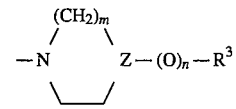

wherein m is integer of 1 to 3, n is 0 or 1, Z is >N–, >CH– or >C=, $R^3$ is diaryl (lower) alkyl optionally substituted with one or more halogen atoms or is condensed heterocyclic group optionally substituted with oxo, with the proviso that (a) at least one of A and B is the group $-Y-R^2$ and (b) when A is hydrogen atom and B is the group $-Y-R^2$, then Z is >CH– or >C= if $R^3$ is condensed heterocyclic group optionally substituted with oxo and n is O or a pharmaceutically acceptable salt thereof. The compounds of the above formula have antiallergic activity.

20 Claims, No Drawings

CARBOSTYRIL DERIVATIVES AND ANTIALLERGIC AGENT

BACKGROUND OF THE INVENTION

Field of the Invention

The present invention relates to novel carbostyril derivatives and an antiallergic agent comprising the carbostyril derivatives.

Various antiallergic agents have already been commercialized. For example, 1-[3-{4-(diphenylmethyl)-1-piperazinyl} propyl]-1,3-dihydro-2H-benzimidazol-2-one (generic name: Oxatomide) is an orally active antiallergic agent.

Since side effects may occur by continuous taking of the same drug or due to idiosyncrasy to the drug, there is a continuous demand for development of new drugs, not excepting antiallergic drugs.

As a result of extensive study seeking novel compounds having potent antiallergic activity, the present inventors have discovered that certain carbostyril derivatives have such activity.

SUMMARY OF THE INVENTION

In one aspect, the present invention relates to a compound of the formula:

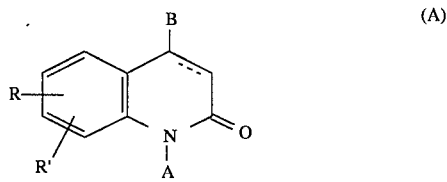

(A)

wherein the symbol of a solid line with a broken line means a single bond or a double bond,
R and R' are independently selected from the group consisting of hydrogen atom, halogen atom, lower alkyl, nitro, unsubstituted amino and substituted amino,
A and B are independently selected from the group consisting of hydrogen atom, lower alkyl optionally substituted with a lower cycloalkyl, aryl optionally substituted with one or more halogen atoms and the group: $-Y-R^2$
wherein Y is lower alkylene and $R^2$ is the group:

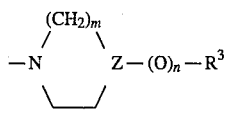

wherein m is integer of 1 to 3, n is integer of 0 or 1, Z is >N-, >CH— or >C=, $R^3$ is diaryl(lower)alkyl optionally substituted with one or more halogen atoms or is condensed heterocyclic group optionally substituted with oxo, with the proviso that
(a) at least one of A and B is the group $-Y-R^2$ and
(b) when A is hydrogen atom and B is the group $-Y-R^2$, then Z is >CH— or >C= if $R^3$ is condensed heterocyclic group optionally substituted with oxo and n is O
or a pharmaceutically acceptable salt thereof.

In another aspect, the present invention relates to a pharmaceutical composition comprising a therapeutically or prophylactically effective amount for the treatment of allergic diseases of at least one compound of formula A or a pharmaceutically acceptable salt thereof in association with a pharmaceutically acceptable carrier or diluent.

In a further aspect, the present invention relates to a method of treating allergic diseases which comprises administering a therapeutically or prophylactically effective amount of at least one compound of formula A or a pharmaceutically acceptable salt thereof to a subject in need of such treatment.

DETAILED DESCRIPTION OF THE INVENTION

Definitions

The terms, symbol and definitions described in this specification are illustrated in more detail as follows:

In the formula (A), the groups represented by R and R' may be the same or different with each other and may attached to any possible position.

The term "halogen atom" includes fluorine, chlorine, bromine and iodine.

The term "lower" throughout the specification is intended to include a group having 1 to 6 carbon atoms unless otherwise specified.

The term "lower alkyl" includes alkyl having 1 to 6 carbon atoms, such as methyl, ethyl, propyl, isopropyl, butyl, isobutyl, tert-butyl, pentyl, 2-methylbutyl, hexyl, etc.

The term "substituted" in "substituted amino" means that the amino group has any substituent.

Such substituent may be lower alkyl as above, acyl such as lower aliphatic acyl (for example, lower alkyl—CO— or lower alkyl—O—COCO—) and benzoyl which may be substituted with lower alkyl. One or two substituents can be present on the amino group.

The term "optionally" means that the event which follows this word may or may not occur.

The term "lower cycloalkyl" includes groups formed by cyclization between carbon atoms of the lower alkyl having more than 3 carbon atoms, such as cyclopropyl, cyclobutyl, cyclopentyl, 2-methylcyclopentyl, cyclohexyl, etc.

When the lower alkyl is substituted with lower cycloalkyl group(s), it is preferred that one or two lower cycloalkyls are present per lower alkyl.

The term "lower alkylene" includes groups formed by removing one hydrogen atom from the lower alkyl as above, such as methylene, ethylene, trimethylene, tetramethylene, pentamethylene, hexamethylene, 2-methyltetramethylene, 1,2-propylene, 1,1-dimethylmethylene, etc.

The term "aryl" includes monocyclic and dicyclic aryl groups, such as phenyl, naphthyl, biphenylyl, as well as groups formed by substituting these groups with at least one lower alkyl, such as tolyl, xylyl, mesityl, cumenyl, 2-methyl- 1-naphthyl, 1-methyl-2-naphthyl, etc.

When the aryl is substituted with halogen atom(s), at least one, for example one, two, three, four or five halogen atoms may be present.

The term "diaryl(lower)alkyl" refers to lower alkyl having two aryls as described above. The two aryls may be present on the same or different carbon atoms.

When the diaryl(lower)alkyl is substituted with halogen atom(s), the halogen atom(s) is usually attached to the aryl group(s) and at least one, for example one, two, three, four, or five halogen atoms may be present. If two or more halogen atoms are present, they may be same or different and may be present on the same or different aryl rings.

The term "condensed heterocyclic group" includes condensed ring of bi- or tri- or more than tri-cyclic system formed by condensing either heterocyclic ring(s) and carbocyclic ring(s) or plurality of heterocyclic rings. The carbocyclic ring includes benzene, cyclopentane, cyclohexane, cycloheptane, etc. The heterocyclic ring includes 5-, 6- and 7-membered rings having one, two, or more than two, for example three or four hetero atoms selected from nitrogen, oxygen and sulfur, with the rest being carbon atoms. Typical heterocyclic groups are pyrrole, furan, thiophene, pyrazole, oxazole, thiazole, triazole, oxadiazole, thiadiazole, pyridine, pyran, thiopyran, pyridazine, oxazine, thiazine, azepine, oxepine, thiepine, diazepine, oxazepine, thiazepine and isomers thereof concerning position(s) of hetero atom(s) as well as partially or completely hydrogenated counterparts thereof. Typical condensed heterocyclic rings are indole, benzofuran, benzothiophene, indazole, quinoline, chromene, cinnoline, benzazepine, benzodiazepine, carbazole, phenoxazine, phenothiazine, dibenzazepine, benzocycloheptathiophene, indolidine, purine, quinolidine, naphtylidine, carboline and isomers concerning position(s) of hetero atom(s) as well as partially or completely hydrogenated counterparts thereof.

When the condensed heterocyclic ring has oxo group(s), the oxo group(s) attaches to carbon atom(s) and one or two oxo groups may be present.

Suitable "pharmaceutically acceptable salt" includes conventional non-toxic salts and may be a salt with an inorganic acid or with an organic acid. The salt with an inorganic acid includes hydrochloride, sulfate, phosphate, etc. The salt with an organic acid includes salts with carboxylic acids such as acetate, propionate, fumarate, maleate, oxalate, succinate, tartrate, malonate, benzoate, etc. and sulfonates such as methanesulfonate, ethanesulfonate, benzenesulfonate, toluenesulfonate, etc.

As used herein, the term "treatment" or "treating" refers to any means of control of a disease in a mammal, including preventing the disease, curing the disease, relieving the disease and arresting or relieving the development of the disease.

The compounds of the formula (A) may be prepared by the following processes.

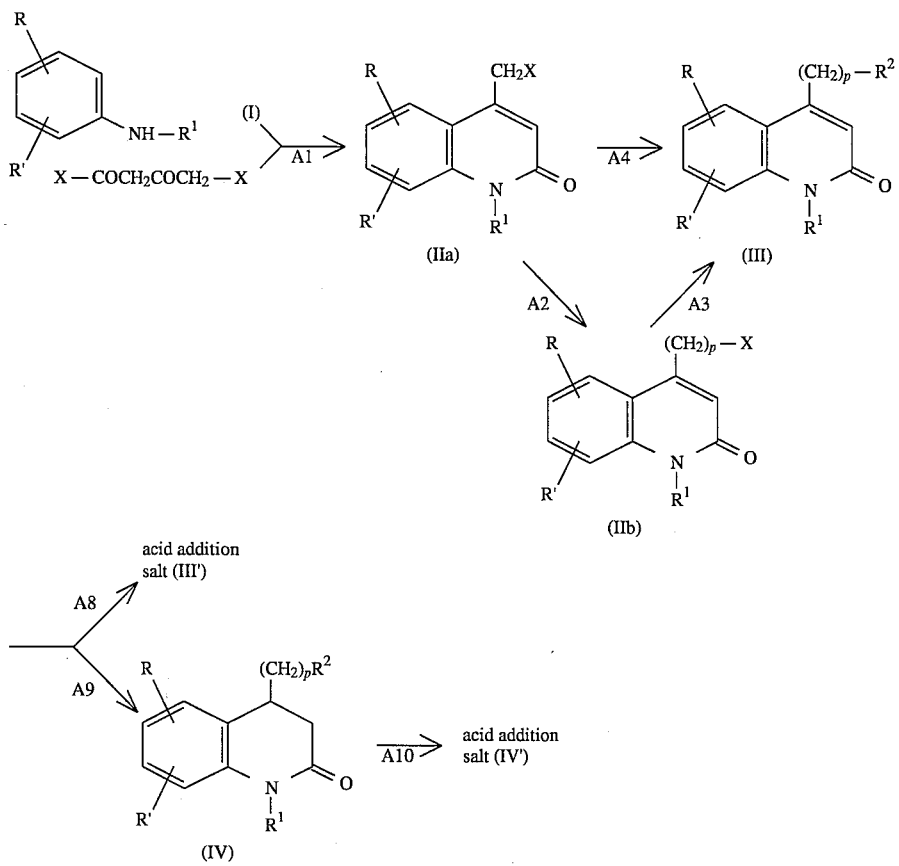

Reaction Scheme II (Process 2):

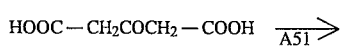

Reaction Scheme II (Process 2):
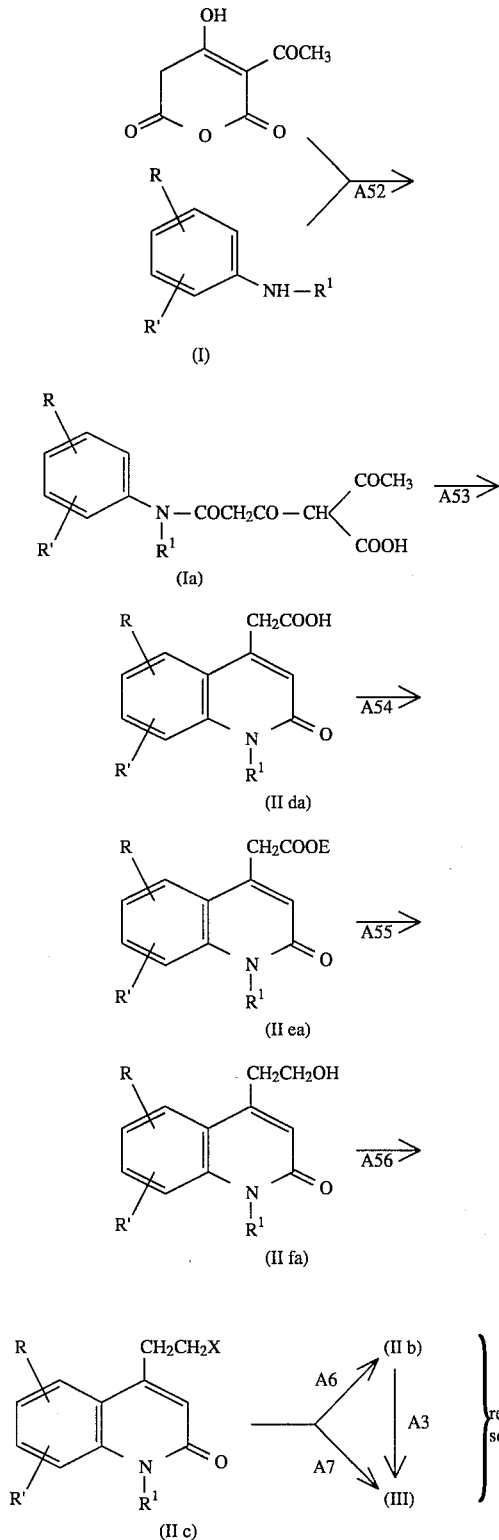
Reaction Scheme III (Process 3):
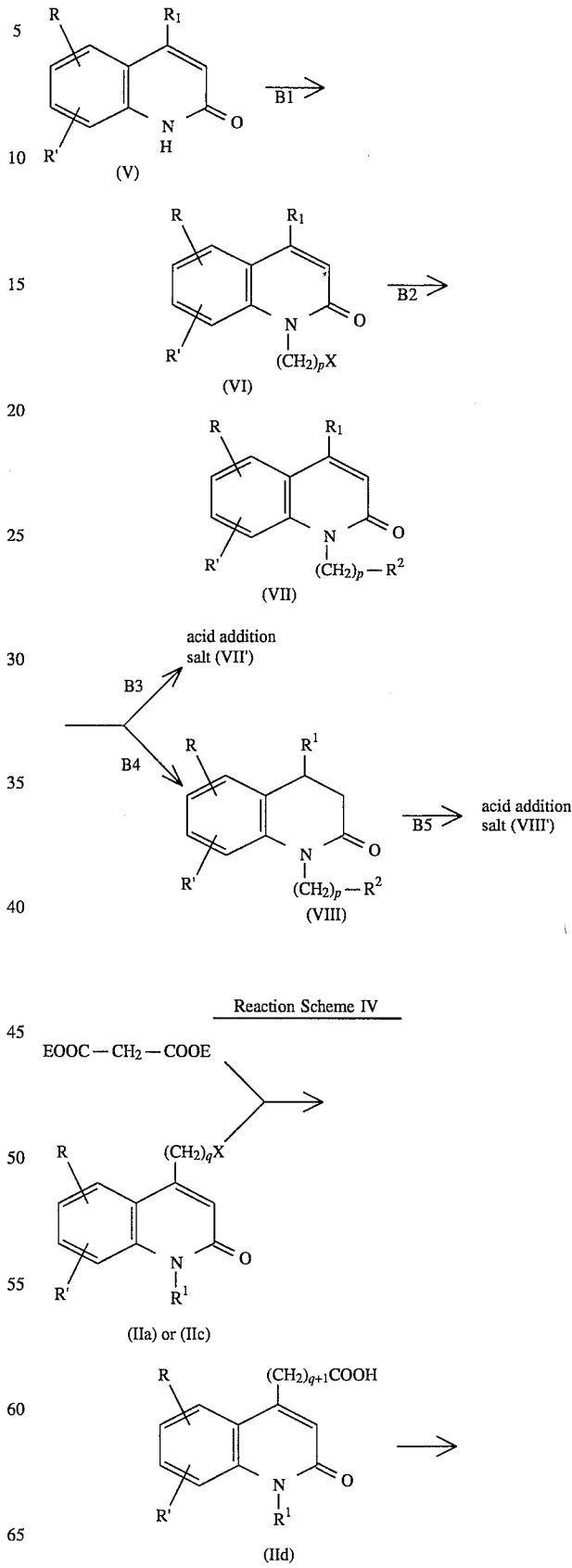

-continued
Reaction Scheme IV
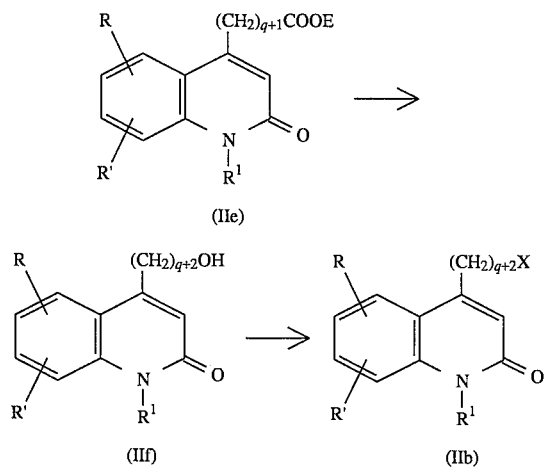
Reaction Scheme V (Process 4):
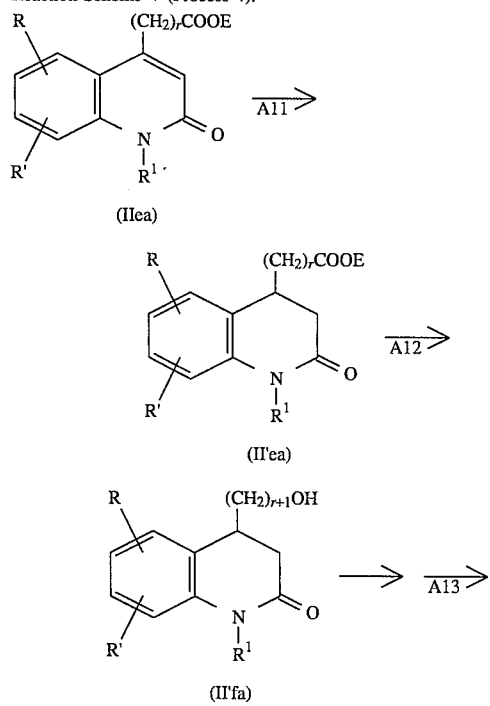
-continued
Reaction Scheme V (Process 4):
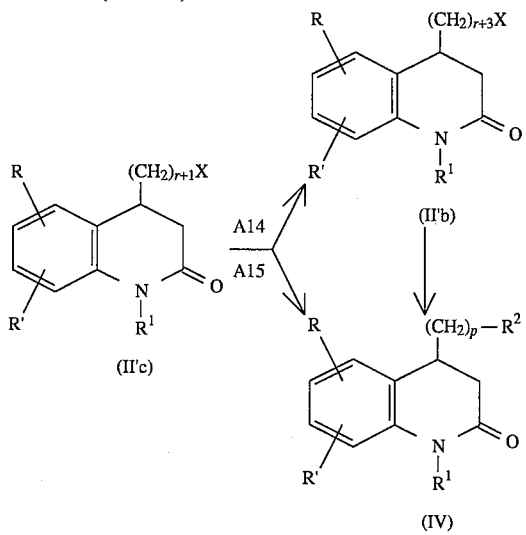
Reaction Scheme VI (Process 5):
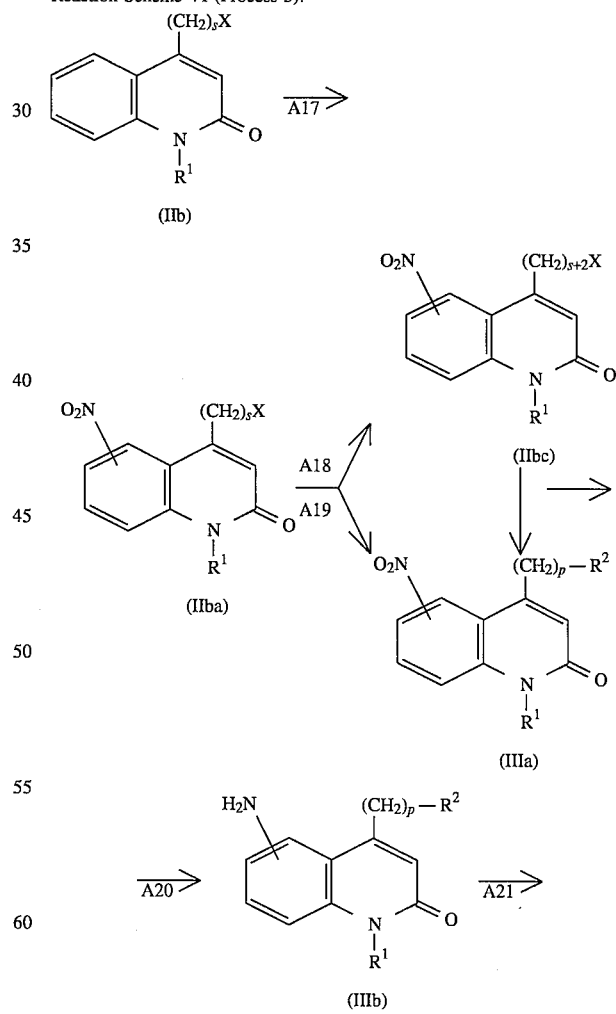

Reaction Scheme VI (Process 5):

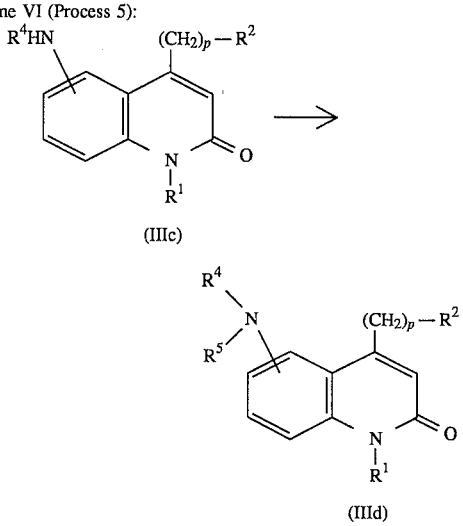

In the above schemes, $R^1$ is the group A or B other than $-Y-R^2$, X is halogen, p is an integer of 1 to 6, q is an integer of 1 to 4, r is an integer of 1 to 3, s is an integer of 1 to 4, E is an ester-forming group (for example lower alkyl), $R^4$ and $R^5$ are substitutents on the amino group and rest are the same as above.

In the Process 1 shown in Scheme I, the cyclization reaction of the compound (I) to the compound (IIa) is carried out by treating the compound (I) with 4-haloacetoacetylhalide (such as 4-bromoacetoacetyl bromide) in the presence of a condensing agent such as concentrated sulfuric acid, polyphosphoric acid, etc. and a base such as triethylamine etc. The reaction can be effected by heating usually in a solvent.

The reaction converting the compound (IIa) into the compound (IIb) is carried out in a manner shown in Scheme IV. Briefly, the compound (IIa) is reacted with a malonic acid diester in the presence of alkaline condensation agent such as sodium hydride in a solvent and then hydrolyzed with acid to give the compound (IId), which is esterified to form the compound (IIe). This is reduced with chemical reducing agent such as lithium aluminum hydride, sodium borohydride etc. to give the alcohol (IIf), which is then halogenated to form the compound (IIb).

The produced compound (IIb) or directly the compound (IIa) is reacted with the compound: $R^2$-H in the presence of a base such as sodium hydrogen carbonate to give the desired compound (III). The reaction is effected by heating usually in a solvent.

The compound (III) may be converted into the acid salt (III') by treating with acid in a conventional manner. Also, the reverse reaction and salt interchange may be carried out.

The compound (III) can be hydrogenated in the presence of a metal catalyst for hydrogenation (such as palladium, Raney nickel etc.) or reduced with nascent hydrogen (such as generated by zinc and acid) to give the compound (IV), which can be converted into the acid salt (IV').

Alternatively, in the Process 2 shown in Scheme II, 3-acetyl-4-hydroxy-5,6-dihydro-2H-pyran-2,6-dione, prepared by treating 3-oxoglutaric acid with acetic anhydride, is reacted with the compound (I) to give the compound (Ia), which is cyclized to form the compound (IIda). This compound is treated in a manner similar to that in the steps in Scheme IV producing the compound (IIb) from the compound (IId) to give the compound (IIb). This compound may be treated in a manner similar to that in the steps in Scheme I producing the compound (III) from the compound (IIa) to give the compound (III).

As a further alternative, in the Process 3 in Scheme III, the compound (V) is reacted with an alkylene dihalide (such as 1-bromo-3-chloropropane) in the presence of an alkaline condensation agent such as sodium hydride to give the compound (VI). The reaction proceeds well at room temperature.

Then the produced compound (VI) is reacted with the compound: $R^2$-H. This reaction can be effected in a manner similar to that in the steps in Scheme I producing the compound (III) from the compound (IIa) or (IIb). The produced compound (VII) may be converted into the acid salt (VII') in the conventional manner. Alternatively, the compound (VII) can be hydrogenated to the compound (VIII), which then may be converted in to acid salt (VIII').

In the Process 4 shown in Scheme V, the ester (IIea) is hydrogenated in the presence of a metal catalyst for hydrogenation (such as platinum oxide, palladium etc.) to give the 3,4-saturated compound (II'ea), which is further reduced with a chemical reducing agent (such as lithium alminium hydride, sodium borohydride etc.) to give the alcohol (II'fa). This compound is halogenated with a halogenating agent for hydroxyl (such as hydrogen halide) to form the compound (II'c). This compound may then be treated in a manner similar to that in the steps in Scheme I producing the compound (III) from the compound (IIa) to give the compound (IV) optionally through the compound (II'b).

In the Process 5 shown in Scheme VI, the compound (IIb) is nitrated to give the compound (IIba), which is then treated with the compound: $R^2$-H in the presence of a base such as sodium hydrogen carbonate in a manner similar to that in steps in Scheme I producing the compound (III) from the compound (IIa) to give the compound (IIIa) optionally through the compound (IIbc). The nitro group in this compound is reduced by hydrogenation in the presence of a metal catalyst for hydrogenation (such as palladium on carbon) into amino group to form the compound (IIIb). The amino group is treated with a substituting reagent: $R^4$X such as alkyl halide or acyl halide (or acid anhydride) under the conditions in which one hydrogen atom on the amino group can be replaced (for example, using about 1 mol of the reagent, at lower temperature, etc.) to give the monosubstituted compound (IIIc). When further reacted with $R^5$X, this compound can be converted into di-substituted compound (IIId). In these reactions, $R^4$ and $R^5$ (as the substituent of the amino group) may be the same or different. Alteratively, when $R^4$ and $R^5$ are the same, these can be introduced simultaneously under the conditions in which two hydrogen atoms on the amino group can be replaced (for example, using about 2 mols or more of the reagent, at a relatively high temperature, etc.).

In the above reactions, any compound can be replaced by equivalent one or any reaction be replaced by equivalent one in order to produce the compounds of the invention.

Since the carbostyril derivatives (A) have superior antiallergic activity (such as anti-asthmatic activity), they are useful in the manufacture of a medicament for treating allergic diseases (such as asthma). Therefore, there is provided also a method for treating allergic diseases (such as asthma) which comprises administering the compound of the formula (A) to a subject suffering from such disease. The above activity can be measured by test method conventionally used for testing such activity.

For prophylactic and/or therapeutic administration, the compound of the present invention may be used in the form of conventional pharmaceutical preparation which contains said compound, as an active ingredient, in admixture with pharmaceutically acceptable carriers such as an organic or inorganic solid or liquid excipient which is suitable for oral, parenteral or external administration. The pharmaceutical preparation may be in solid form such as capsule, tablet, dragee, ointment or suppository etc. or in liquid form such as solution, suspension or emulsion etc. In needed, auxiliary substances, stabilizing agents, wetting or emulsifying agents, buffers and the commonly used additives may be included in the above preparation.

While the dosage of the compound (A) in the above use may vary depending on the age and conditions of the patient, compound used, route of administration and desired treatment, satisfactory results will be obtained at a dose of about 0.1 to 100 (preferably 0.5 to 50)mg/kg of the active compound conveniently administered in 2 to 4 divided dosages a day or in a sustained release form.

Example

The present invention will now be further illustrated by reference to the following various example, which are not, however, intended to limit the scope of the invention.

| Formulation Example 1 (Tablet) | per Tablet |
| --- | --- |
| (1) Active ingredient | 50 mg |
| (2) Lactose | 94.4 mg |
| (3) Crystalline cellulose | 40 mg |
| (4) Corn starch | 10 mg |
| (5) Tocopherol | 2 mg |
| (6) Hydroxypropylcellulose | 2 mg |
| (7) Magnesium stearate | 1.6 mg |
| total | 200 mg |

Into a 5%ethanol solution of (6) was dissolved (5) and (1) was dispersed in the solution. The suspension was added to a mixture of (2)–(4), and the produced mixture was kneaded, then dried and granulated, after which (7) was added thereto. The mixture was shaped by compressed 200 mg tablets.

| Formulation Example (soft capsule) | per capsule |
| --- | --- |
| (1) Active ingredient | 100 mg |
| (2) Fatty acid triglyceride | 100 mg |
| (3) Macrogol 400 | 10 mg |
| (4) Dibutylhydroxyanisole | 0.02 mg |
| total | about 210 mg |

A solution of (4) in (3) was added to a mixture of (1) and (2). The mixture was thoroughly stirred to form a homogeneous capsule content. Between gelatin sheets prepared from gelatin and glycerin was filled content 210 mg per capsule and the produced capsules were dried to give final soft capsules.

| Formulation Example 3 (syrup) | |
| --- | --- |
| (1) Active ingredient | 200 mg |
| (2) Propylenegrycol | 10 g |
| (3) Sugar | 30 g |
| (4) D-sorbitol (70% solution) | 10 g |
| (5) Tragacanth gum | 5 g |
| (6) Sorbitan fatty acid ester (SO-10) | 1 g |
| (7) P.O.E sorbitan fatty acid ester (TO-10M) | 1 g |
| (8) Methyl p-hydroxybenzoate | 0.1 g |

| -continued | |
| --- | --- |
| Formulation Example 3 (syrup) | |
| (9) Butyl p-hydroxybenzoate | 0.1 g |
| (10) Dibutyl hydroxytoluene | 0.01 g |
| (11) Citric acid | q.s. |
| (12) Perfume | 0.01 g |
| (13) Purified water | q.s. |
| total | 100 ml |

Into (2) were dissolved (8), (9) and (10), and (6) and (7) were added to the solution and dispersed. To this dispersion, (1) was added and the mixture was stirred to form a homogeneous product. To the mixture was added slowly a syrup consisting of (3) (4) and (13) (a portion) under vigorous stirring (homogenizer) to give the emulsion. Furthermore, pH of the mixture was adjusted by adding aqueous solution of (11) and (12) was added thereto. Then the rest of (13) was added to make the total volume to 100 ml. All the operations were performed under nitrogen stream to give a stable syrup.

In Formulation Examples 1–3 as described above, the active ingredient may be any one of compounds used for this invention.

Reference Example 1 (method A2, A6)

Preparation of 1,2-dihydro-2-oxo-4-quinolinebutanoic acid

To a suspension of sodium hydride (2.03 g, 60%suspension in oil, 50.78 mmol) in dry dimethylformamide (10 ml) was added dropwise diethyl malonate (7.75 ml, 50.78 mmol) in dry dimethylformamide (10 ml) under ice-cooling and the mixture was stirred for 20 minutes. Under the same conditions, 4-(2-bromoethyl)-2(1H)-quinolinone (II-2) (6.4 g, 25.39 mmol) and dry dimethylformamide (50 ml) were added to the mixture. The mixture was brought to back to room temperature and the reaction was continued for 16 hours.

Water (200 ml) was poured to the reaction mixture and the mixture was acidified (to pH around 4) with 2N-HCl and extracted with chloroform (300 ml×1). Chloroform layer was separated and the solvent was distilled off. Ether (300 ml) was poured to the residue and the mixture was washed with water (300 ml×1) and dried (anhydrous $MgSO_4$). After removing the solvent, the residue was dissolved in developing solvent (chloroform: methanol=95:5) and purified by silica gel column chromatography. Colorless solution first eluted was collected and the solvent was distilled off from the solution to give white solid (4.18 g). The solid (4.18 g) was suspended in 20%HCl solution (40 ml) and the suspension was refluxed for 16 hours. The reaction mixture was cooled in ice bath and then the separated solid was filtered off by aspiration. The residue was washed with water, methanol and then acetone, and dried to give the entitled compound (2.83 g, yield 48.2% as white crystals of mp 265°–267° C. (after recrystallization from ethanol-$H_{20}$)).

In a manner similar to that described above, 1,2-dihydro-2-oxo-4-quinolinepentanoic acid was prepared.

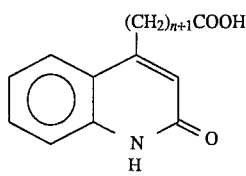

| n | Yield (%) | Formula (MW) | FAB-MS(m/z) | mp (solvent) | State |
|---|---|---|---|---|---|
| 2 | 48.2 | $C_{13}H_{13}NO_3$ (231.24) | 232 (M + H) | 265–267° C. (EtOH—$H_2O$) | white crystals |
| 3 | 45.1 | $C_{14}H_{15}NO_3$ (245.27) | 246 (M + H) | 231–233° C. (MeOH—$H_2O$) | white crystals |

Reference Example 2 (method A2, A6)
Preparation of methyl 1,2-dihydro-2-oxo-4-quinolinebutanoate 1,2-dihydro-2-oxo-4-quinolinebutanoic acid (1.86 g, 8.04 mmol) was suspended in 5% methanol-HCl (45 ml) and the suspension was refluxed for 1 hour. The solvent was distilled off from the reaction mixture. Water (200 ml) was poured into the residue and then separated solid was filtered by aspiration. The residue was washed with water and then dried under reduced pressure. The obtained solid was dissolved in developing solvent (chloroform: methanol=9:1) and the mixture was purified by silica gel column chromatography. Colorless solution first eluted was collected and the solvent was distilled off from the solution to give the entitled compound (1.71 g, yield 86.9% as white crystals of mp 161°–162° C. (after recrystallization from methanol-$H_2O$)).

In a manner similar to that described above, methyl 1,2-dihydro-2-oxo-4-quinolinepentanoate was prepared.

aspiration. The residue was washed with water, and dried to give the entitled compound (1.33 g, yield 93.6% as white crystals of mp 152°–154 ° C. (after recrystallization from methanol-$H_2O$)).

In a manner similar to that described above, 4-(5-hydroxypentyl)-2(1H)-quinolinone was prepared.

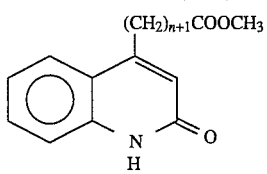

| n | Yield (%) | Formula (MW) | EI-MS (m/s) | mp (solvent) | State |
|---|---|---|---|---|---|
| 2 | 86.9 | $C_{14}H_{15}NO_3$ (245.27) | 245 ($M^+$) | 161–162° C. (MeOH—$H_2O$) | white crystals |
| 3 | 82.2 | $C_{15}H_{17}NO_3$ (259.30) | 259 ($M^+$) | 96–98° C. (MeOH—$H_2O$) | white crystals |

Reference Example 3 (method A55)
Preparation of 4-(4-hydroxybutyl)-2(1H)-quinolinone Methyl 1,2-dihydro-2-oxo-4-quinolinebutanoate (1.60 g, 6.52 mmol) was suspended in dry tetrahydrofuran (60 ml). Lithium aluminum hydride 247.4 mg (6.52 mmol) was added to the suspension in small portions under ice-cooling. The reaction mixture was brought back to room temperature and the reaction was continued for 16 hours. Water was carefully poured into the reaction mixture under ice-cooling to decompose excess lithium aluminum hydride. To the mixture was added sulfuric acid (concentrated sulfuric acid 1 ml/water 100 ml) and then tetrahydrofuran was distilled off under reduced pressure. The separated solid was filtered by

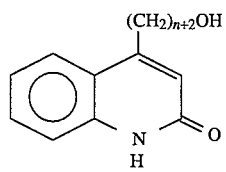

| n | Yield (%) | Formula (MW) | EI-MS (m/z) | mp (solvent) | State |
|---|---|---|---|---|---|
| 2 | 93.6 | $C_{13}H_{15}NO_2$ (217.26) | 217 ($M^+$) | 152–154° C. (MeOH—$H_2O$) | white crystals |
| 3 | 60.5 | $C_{14}H_{17}NO_2$ (231.29) | 231 ($M^+$) | 135–137° C. (MeOH—$H_2O$) | white crystals |

Reference Example 4 (method A2, A6)
Preparation of 4-(4-bromobutyl)-2(1H)-quinolinone (II-4)

4-(4-hydroxybutyl)-2(1H)-quinolinone (1 g, 4.60 mmol) was suspended in 47%hydrobromic acid solution (20 ml) and the mixture was refluxed for 16 hours. The reaction mixture was cooled in ice bath and the separated solid was filtered off by aspiration. The residue was washed with water and recrystallized with methanol (with treatment with activated carbon) to give the entitled compound (II-4) as white crystals ( 790 mg, yield 61.3%, mp 156°–158 ° C. (methanol)).

In a manner similar to that described above, the following compound was prepared;

4-(5-bromopentyl)-2(1H)-quinolinone (II-5)
4-(2-bromoethyl)-1-methyl-2(1H)-quinolinone (II-7)
7-bromo-4-(2-bromoethyl)-2(1H)-quinolinone (II-8)
4-(2-bromoethyl)-6-methyl-2(1H)-quinolinone (II-10)
4-(2-bromoethyl)-8-methyl-2(1H)-quinolinone (II-11)
4-(2-bromoethyl)-7-methyl-2(1H)-quinolinone (II-12)
4-(2-bromoethyl)-6-(1-methylethyl)-2(1H)-quinolinone (II-13)
4-(2-bromoethyl)-5,7-dimethyl-2(1H)-quinolinone (II-14)
4-(2-bromoethyl)-8-(1-methylethyl)-2(1H)-quinolinone (II-15).

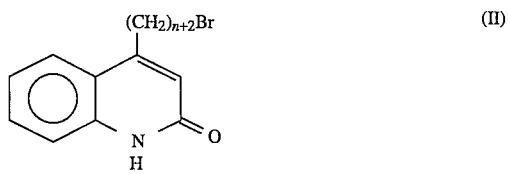
(II)

| n | Yield (%) | Formula (MW) | EI-MS (m/z) | mp (solvent) | State |
|---|---|---|---|---|---|
| 2 | 61.3 | $C_{13}H_{14}BrNO$ 280.16 | 279 ($M^+$) | 156–158° C. (MeOH) | white crystals |
| 3 | 37.7 | $C_{14}H_{16}BrNO$ (294.19) | 293 ($M^+$) | 150–152° C. (MeOH) | white crystals |

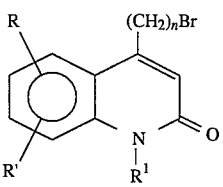
(II)

| No. | n | R | R' | $R^1$ | Yield (%) | Formula (MW) | FAB-MS (m/z) | m.p. (solvent) | State |
|---|---|---|---|---|---|---|---|---|---|
| II-7 | 2 | H | H | $CH_3$ | 71.9 | $C_{12}H_{12}BrNO$ (266.14) | 266 (M + H) | 95–96° C. (benzene-hexane) | white crystals |
| II-8 | 2 | 7-Br | " | H | 61.7 | $C_{11}H_9Br_2NO$ (331.02) | 330 (M + H) | 201–202° C. (MeOH) | white crystals |
| II-10 | 2 | 6-$CH_3$ | " | " | 68.8 | $C_{12}H_{12}BrNO$ (266.14) | 266 (M + H) | 191–193° C. (EtOH) | white crystals |
| II-11 | 2 | 8-$CH_3$ | " | " | 70.4 | $C_{12}H_{12}BrNO$ | 266 | 186–188° C. | white |

-continued

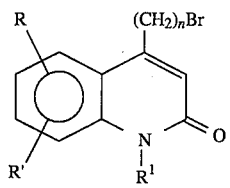

(II)

| No. | n | R | R' | R¹ | Yield (%) | Formula (MW) | FAB-MS (m/z) | m.p. (solvent) | State |
|---|---|---|---|---|---|---|---|---|---|
| II-12 | 2 | 7-CH₃ | H | H | 64.1 | C₁₂H₁₂BrNO (266.14) | (M + H) 266 | (DMF-H₂O) 209–210° C. | white crystals |
| II-13 | 2 | 6-i-Pr | " | " | 29.0 | C₁₄H₁₆BrNO (294.19) | (M + H) 294 | (MeOH-THF) 145–147° C. | pale yellow crystals |
| II-14 | 2 | 5-CH₃ | 7-CH3 | " | 57.5 | C₁₃H₁₄BrNO (280.16) | (M + H) 280 | (benzene-hexane) 197–198° C. | white crystals |
| II-15 | 2 | 8-i-Pr | H | " | 53.1 | C₁₄H₁₆BrNO (294.19) | (M + H) 294 | (MeOH-THF-H₂O) 161–163° C. (EtOH) | white crystals |

In addition, 4-bromomethyl-2(1H)-quinolinone (II- 1), 4-(2-bromoethyl)-2(1H)-quinolinone (II-2) and 4-(3-bromopropyl)- 2(1H)-quinolinone (II-3) were prepared according to Chemical and Pharmaceutical Bull., 33(9), 3775–3786(1985).

Reference Example 5 (method A1)
Preparation of 4-bromomethyl-1-methyl-2(1H)-quinolinone (II-6)

Bromine (9.6 g, 60 mmol) was added to a solution of diketene (5.04 g, 60 mmol) in Carbon tetrachloride (80 ml). Separately, N-methylaniline (6.43 g, 60 mmol) and triethylamine (6.0 g, 60 mmol) were dissolved in chloroform (300 ml) and the first mixture was added dropwise thereto. After the completion of the addition, the reaction mixture was stirred at 0 ° C. for 15 minutes and washed with water (100 ml). The organic layer was separated, dried over magnesium sulfate and the solvent was distilled off. The residue was fractioned by silica gel chromatography (developing solution; benzene: ethyl acetate=4:1) to give the intermediate. To the intermediate was added sulfuric acid (40 ml) under stirring and the mixture was allowed to stand for 18 hours. The reaction mixture was poured into ice-water and the separated solid was filtered off. The solid was washed with water, dried and then recrystallized from ethanol to give the desired product (II-6) (3.6 g) as pale yellow crystals (mp 188°–190 ° C. (ethanol), yield 24%).

Reference Example 6 (method A52, A53)
Preparation of 1,2-dihydro-l-methyl-2-oxo-4-quinolineacetic acid To a suspension of 3-acetyl-tetrahydropyran- 2,4,6-trione (10 g, 58.78 mmol) and acetic acid (20 ml) was added dropwise N-methylaniline (6.5 ml, 58.78 mmol) at room temperature. The reaction was continuted for 30 minutes. The reaction mixture was poured into ice-water (500 ml) and then the separated solid was filtered off by aspiration. The residue was washed with water and ether and dried. The obtained pale yellow solid (11.01 g) was added to concentrated sulfuric acid (50 ml) and the mixture was allowed to stand at room temperature for 16 hours. The reaction mixture was poured into ice-water (500 ml) and then the separated solid was filtered off by aspiration. The residue was washed with water and recrystallized to give the entitled compound (4.35 g, mp 199°–201 ° C. (methanol), yield 32.0%).

In addition, 3-acetyl-tetrahydropyran-2,4,6-trione was prepared according to J. Chem. Soc., (c), 2721–26 (1971).

Reference Example 7 (method A52, A53, A54)
Preparation of methyl 7-bromo-1,2-dihydro-2-oxo-4-quinoline acetate To a suspension of 3-acetyl-tetrahydropyran- 2,4,6-trione (25 g, 0.147 mol) and acetic acid (50 ml) was added a solution of m-bromoaniline (25.3 g, 0.147 mol) in acetic acid (30 ml) at room temperature. The reaction was continuted under the same conditions for 30 minutes. The reaction mixture was poured into ice-water (1 L) and then the separated solid was filtered off by aspiration. The residue was washed with water and dried. The obtained solid (54 g) was added in small portions to concentrated sulfuric acid (250 ml) and stirred at room temperature for 16 hours. The reaction mixture was poured into ice-water and then the separated solid was filtered off by aspiration. The residue was washed with methanol and acetone and then dried to give 7-bromo-l,2-dihydro-2-oxo-4-quinolineacetic acid (19.5 g) as a white solid. The solid (19.5 g) was suspended in methanol 500 ml. Thionyl chloride 15.1 ml (207 mmol) was added dropwise thereto at room temperature and the mixture was refluxed for 0.5 hour. The reaction mixture was poured into ice-water (1 L) and then the separated solid was filtered off by aspiration. The residue was washed with water and recrystallized from methanol to give the entitled compound as white crystals (mp 208°–210 ° C. (from methanol), 13.6 g, yield 31.2 %).

Reference Example 8 (method A52, A53, A54)
Preparation of methyl 1, 2-dihydro-6-methyl-2-oxo-4-quinoline acetate To a suspension of 3-acetyl-tetrahydropyran- 2,4,6-trione (21.1 g, 124 mmol) in acetic acid (22 ml) was added a solution of p-toluidine (13.8 g, 129 mmol) in acetic acid (20 ml) and the mixture was stirred at room temperature for 10 minutes. The reaction mixture was poured into water and the separated solid was filtered off. The solid was washed with water, dried and then added in small portions to concentrated sulfuric acid (140 ml). The mixture was stirred for 10 minutes and then allowed to stand at room temperature for 16 hours. The reaction mixture was poured into ice-water and the separated solid was filtered off. The solid was washed with water, methanol and acetone, dried and treated with 5%hydogen chloride/methanol (250 ml). The mixture was refluxed for 1 hour. Methanol was distilled off from the reaction mixture. Water was added to the residue and the separated solid was filtered off. The solid was washed with water, dried and then recrystallized from a mixture of methanol, tetrahydrofuran and water to give the entitled compound (14.8 g) as white crystals (mp 202°–204 ° C. (methanol/tetrahydrofuran/water), yield 51.6%).

In a manner similar to that described above, the following compounds were prepared;

Methyl 1,2-dihydro-8-methyl-2-oxo-4-quinolineacetate

Methyl 1,2-dihydro-7-methyl-2-oxo-4-quinolineacetate

Methyl 1,2-dihydro-6-(1-methylethyl)-2-oxo-4-quinolineacetate

Methyl 1,2-dihydro-5,7-dimethyl-2-oxo-4-quinolineacetate

Methyl 1,2-dihydro-8-(1-methylethyl)-2-oxo-4-quinolineacetate.

Example 1 (method A7)
Preparation of 4-[2-[4-(1H-indol-3-yl)-1-piperidinyl] ethyl]-2-(1H)-quinolinone (III-2)

A. A suspension of 4-(2-bromethyl)-2-(1H)-quinolinone (II-2) (500 mg, 1.98 mmol), 3-(4-piperidinyl)- 1H-indole (396.5 mg, 1.98 mmol) and sodium hydrogencarbonate (249.5 mg, 2.97 mmol) in dry dimethylformamide (5 ml) was react at 80 ° C. for 5 hours. The reaction mixture was poured into ice-water and the separated solid was filtered by aspiration. The residue was washed with water and recrystallized from methanol/tetrahydrofuran/water to give the desired product (336 mg) (III-2) as pale yellow crystals (mp 259°–260 ° C. (methanol/tetrahydrofuran/water)). Yield 45.7%.

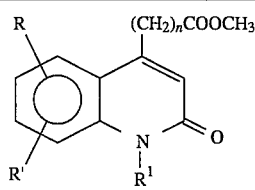

| n | R | R' | R$^1$ | Yield (%) | Formula (MW) | FAB-MS (m/z) | m.p. (solvent) | State |
|---|---|---|---|---|---|---|---|---|
| 1 | 6-CH$_3$ | H | H | 51.6 | C$_{13}$H$_{13}$NO$_3$ (231.25) | 232 (M + H) | 202~204° C. (MeOH-THF-H$_2$O) | white crystals |
| 1 | 8-CH$_3$ | " | " | 26.5 | C$_{13}$H$_{13}$NO$_3$ (231.25) | 232 (M + H) | 210–212° C. (MeOH) | white crystals |
| 1 | 7-CH$_3$ | " | " | 48.8 | C$_{13}$H$_{13}$NO$_3$ (231.25) | 232 (M + H) | 207~209° C. (MeOH) | white crystals |
| 1 | 6-i-Pr | " | " | 33.6 | C$_{15}$H$_{17}$NO$_3$ (259.30) | 260 (M + H) | 117~119° C. (MeOH-H$_2$O) | pale yellow crystals |
| 1 | 5-CH$_3$ | 7-CH$_3$ | " | 42.7 | C$_{14}$H$_{15}$NO$_3$ (245.28) | 245 (M + H) | 210–212° C. (MeOH-THF-H$_2$O) | white crystals |
| 1 | 8-i-Pr | H | " | 46.0 | C$_{15}$H$_{17}$NO$_3$ (259.30) | 260 (M + H) | 133~135° C. (EtOH) | white crystals |

Reference Example 9 (method A55)
Preparation of 4-(2-hydroxyethyl)-1-methyl-2(1H)-quinolinone Methyl 1,2-dihydro-1-methyl-2-oxo-4-quinoline acetate (2.35 g, 10.16 mmol) was dissolved in dry tetrahydrofuran (50 ml) and sodium borohydride (1.92 g, 50.8 mmol) was added thereto. The mixture was refluxed. Under the same conditions, methanol (19 ml) was slowly added dropwise thereto (over 1 hour) and the mixture was refluxed for 1 hour. To the reaction mixture was acidified (pH about 2) with 2N-hydrochloric acid. The solvent was distilled off and water (300 ml) was poured to the residue. The mixture was extracted with chloroform (300 ml×3). The organic layer was separated, dried (over magnesium sulfate) and the solvent was distilled off. The residue was crystallized with ether to give the entitled compound (1.80 g) as white crystals (yield 87.2%, mp 149°–150 ° C. (chloroform—hexane)).

In a manner similar to that described above, the following compounds were prepared;

7-bromo-4-(2-hydroxyethyl)-2(1H)-quinolinone 4-(2-hydroxyethyl)-6-methyl-2(1H)-quinolinone 4-(2-hydroxyethyl)-8-methyl-2(1H)-quinolinone 4-(2-hydroxyethyl)-7-methyl-2(1H)-quinolinone 4-(2-hydroxyethyl)-6-(1-methylethyl)-2(1H)-quinolinone 5,7-dimethyl-4-(2-hydroxyethyl)-2(1H)-quinolinone 4-(2-hydroxyethyl)-8-(1-methylethyl)-2(1H)-quinolinone.

B. To a suspension of 4-(2-bromoethyl-2(1H)-quinolinone (II-2) (30 g, 119 mmol) and 3-(4-piperidinyl)- 1H-indole (23.8 g, 119 mmol) in dry dimethylformamide 300 ml was added triethylamine (33 ml, 238 mmol) at room temperature and the mixture was allowed to react under the same conditions for 48 hours. Water (600 ml) was poured into the reaction mixture and the mixture was stirred for 15 minutes at room temperature. The separated solid was filtered off by aspiration. The solid was washed with water, dried under reduced pressure and recrystallized with methanol/tetrahydrofuran/water to give the desired product (103 g) (III-2) as white solid (mp 259°–259.5 ° C. (methanol/tetrahydrofuran/water), yield 70.9 %).

In a manner similar to that described above, the following compounds were prepared;

4-[[4-(1H-indol-3-yl)-1-piperidinyl]methyl]-2(1H)-quinolinone (III-1),

4-[3-[4-(1H-indol-3-yl)-1-piperidinyl]propyl]-2(1H)-quinolinone (III-3),

4-[4-[4-(1H-indol-3-yl)-1-piperidinyl]butyl]-2(1H)-quinolinone (III-4),

4-[5-[4-(1H-indol-3-yl)-1-piperidinyl]pentyl]-2(1H)-quinolinone (III-5),

4-[[4-(diphenylmethyl)-1-piperazinyl]methyl]-2(1H)-quinolinone (III-6),

4-[2-[4-(diphenylmethyl)-1-piperazinyl]ethyl]-2(1H)-quinolinone (III-7),

4-[3-[4-(diphenylmethyl)-1-piperazinyl]propyl]-2(1H)-quinolinone (III-8),

4-[2-[4-(4-chlorophenyl)-phenylmethyl]- 1-piperazinyl] ethyl]-2(1H)-quinolinone (III-9),
4-[[4-(diphenylmethoxy)-1-piperidinyl]methyl]-2(1H)-quinolinone (III-10),
4-[2-[4-(diphenylmethoxy)-1-piperidinyl]ethyl]-2(1H)-quinolinone (III-11),
4-[3-[4-(diphenylmethoxy)-1-piperidinyl]propyl]-2(1H)-quinolinone (III-12),
4, 9-dihydro-4-[1-[(1, 2-dihydro-2-oxo-4-quinolyl)methyl]-4-piperidinylidene]-10H-benzo[4, 5]cyclohepta[1,2-b] thiophen-10-one (III-13),
4, 9-dihydro-4-[1-[2-(1, 2-dihydro-2-oxo-4-quinolyl)ethyl]-4-piperidinylidene]-10H-benzo[4, 5]cyclohepta[1,2-b ]thiophen-10-one (III-14),
4,9-dihydro-4-[1-[3-(1, 2-dihydro-2-oxo-4-quinolyl)propyl]- 4-piperidinylidene]-10H-benzo[4, 5]cyclohepta[1,2-b] thiophen-10-one (III-15)
7-bromo-4-[2-[4-(1H-indol-3-yl)-1-piperidinyl]ethyl]-2(1H)-quinolinone (III-18)
4-[2-[4-(1H-indol-3-yl)-1-piperidinyl]ethyl]-6-methyl-2(1H)-quinolinone (III-23)
4-[2-[4-(1H-indol-3-yl)-1-piperidinyl]ethyl]-8- methyl-2-(1H)-quinolinone (III-24)
4-[2-[4-(1H-indol-3-yl)-1-piperidinyl]ethyl]-7-methyl-2-(1H)-quinolinone (III-25)
4-[2-[4-(1H-indol-3-yl)-1-piperidinyl]ethyl]-6-(1-methyl-ethyl)- 2(1H)-quinolinone (III-26)
5,7-dimethyl-4-[2-[4-(1H-indol-3-yl)-1-piperidinyl]ethyl]-2(1H)-quinolinone (III-27)
4-[2-[4-(1H-indol-3-yl)-1-piperidinyl]ethyl]-8-(1-methyl-ethyl)- 2(1H)-quinolinone (III-28).

Example 2 (method A4)
Preparation of 4-[[4-(1H-indol-3-yl)-l-piperidinyl]methyl]-1-methyl-2(1H)-quinolinone (III-16)

A suspension of 4-bromomethyl-l-methyl-2(1H)-quinolinone (756 mg, 3 mmol), 3-(4-piperidinyl)-1H-indole (600 mg, 3 mmol) and sodium hydrogencarbonate (378 mg, 4.5 mmol) in dry dimethylformamide (5 ml) was allowed to react at 80 ° C. for 2 hours. The reaction mixture was poured into water and the separated solid was filtered off. The solid was washed with water, dried and then recrystallized from methanol/tetrahydrofuran to give the desired product (III 16) (720 mg, yield 65%). Mp 228°–229 ° C. (methanol/tetrahydrofuran).

Example 3 (method A4)
Preparation of 4-[2-[4-(1H-indol-3-yl)-1-piperidinyl] ethyl] -1-methyl-2(1H)-quinolinone (III-17)

A mixture of 4-(2-bromoethyl)-1-methyl-2(1H)-quinolinone (II-7) (500 mg, 1.88 mmol), 3-(4-piperidinyl)- 1H-indole (376.5 mg, 1.88 mmol) and sodium hydrogencarbonate (236.9 mg, 2.82 mmol) in dry dimethylformamide 5 ml was allowed to react 90 ° C. for 3.5 hours. The reaction mixture was poured into ice-water and then the separated solid was filtered off by aspiration. The solid was washed with water and dried. The obtained solid was dissolved in developing solvent (chloroform: methanol=95:5) and purified by silica gel column chromatography. After removing first eluted impurity, a colorless solution was collected and the solvent was distilled off to give the desired product (III-17) (536 mg) as white crystals (yield 74.0%, mp 79°–81 ° C. (benzene-hexane)).

Example 4 (method A8)
Preparation of 4-[2-[4-(1H-indol-3-yl-piperidinyl]ethyl]-2(1H)-quinolinone hydrochloride (III'-2-a)

A mixture of 4-[2-[4-(1H-indol-3-yl)-1 piperidinyl]ethyl] -2(1H)-quinolinone (III-2) (500 mg, 1.35 mmol) in methanol (15 ml) and tetrahydrofuran (25 ml) was refluxed until solids were dissolved.

Under the same conditions, the solution was acidified (pH about 2) with 5%methanoic hydrogen chloride and then the solvent was distilled off from the reaction mixture. The residue was crystallized with acetone and then recrystallized from methanol to give the desired product (III'-2-a) (248 mg) as pale yellow crystals (290°– 293° C., yield 45.0%)

Example 5 (method A8)
Preparation of 4-[2-[4-(1H-indole-3-yl)-1-piperidinyl] ethyl]-2(1H)-quinolinone maleate (III'-2-b)

A mixture of 4-[2-[4-(1H-indole-3-yl)-1-piperidinyl] ethyl]-2(1H)-quinolinone (III-2) (500 mg, 1.35 mmol) in methanol (15 ml) and tetrahydrofuran (25 ml) was refluxed until solids were dissolved. Under the same conditions, maleic acid (172.9 mg, 1.49 mmol) in methanol (10 ml) was added thereto and then the solvent was distilled off from the reaction mixture. The residue was crystallized with acetone and then recrystallized from acetone-methanol to give the desired product (III'-2-b) (404 mg) as pale yellow crystals (138°–141 ° C., yield 61.4%)

Example 6 (method A8)
Preparation of 4-[2-[4-(1H-indol-3-yl)-1-piperidinyl] ethyl] -2-(1H)-quinolinone fumarate (III'-2-c)

A mixture of 4-[2-[4-(1H-indol-3-yl)-1-piperidinyl] ethyl]-2(1H)-quinoline (III-2) (500 mg, 1.35 mmol) in methanol (15 ml) and tetrahydrofuran (25 ml) was refluxed until solids were dissolved. Under the same conditions, a solution of fumaric acid (173 mg, 1.49 mmol) in methanol (5 ml) was added thereto and then the mixture was refluxed for 10 minutes. The reaction mixture was cooled to room temperature and then the separated solid was filtered off by aspiration. The solid was washed with methanol and dried to give the desired product (538 mg) (III'-2-c) as white crystals (mp 262°–264 ° C., yield 82.0%).

Reference Example 10 (method B1)
Preparation of 1-(3-chloropropyl)-6-methyl-2(1H)-quinolinone (VI-2)

To a suspension of 6-methyl-2(1H)-quinoline (V-2) (1.18 g, 7.42 mmol) in dry dimethylformamide (10 ml) was added sodium hydride (60%dispersion in oil) (356 mg, 8.90 mmol) and the mixture was stirred for 10 minutes. To this suspension, 1-bromo-3-chloropropane 0.73 ml (7.42 mmol) was added and the reaction mixture was stirred at room temperature for 1 hour. Then the reaction mixture was poured into water and extracted with ether. Organic layer was dried over anhydrous magnesium sulfate and the solvent was distilled off. The residue was purified by silica gel column chromatography (developing solvent: benzene: ethyl acetate= 7:3). The obtained product was recrystallized from benzene-hexane to give the desired product (VI-2) (780 mg, yield 45%).

In a manner similar to that described above, 6-chloro-1-(3-chloropropyl)-2(1H)-quinolinone (VI-1) and 1-( 3-chloropropyl)-2(1H)-quinolinone (VI-3) were prepared.

Reference Example 11 (method B1)
Preparation of 1-(3-chloropropyl)-4-methyl-2(1H)-quinolinone compound (VI-4)

To a suspension of sodium hydride (150 mg, 60%dispersion in oil, 3.78 mmol) in dry dimethylformamide (7 ml) added dropwise a solution of 2-hydroxy-4-methylquinoline (V-4) (500 mg, 3.14 mmol) in dry dimethylformamide (17 ml) under ice-cooling. The mixture was brought back to room temperature and stirred for 20 minutes. To this mixture, 1-bromo-3-chloropropane (0.4 ml, 4.08 mmol) was added at room temperature and the reaction mixture was stirred at the same temperature for 5 hours. After the completion of the reaction, the reaction mixture was poured into ice-water and extracted with ether (twice). The organic layer was washed with water, then dried and the solvent was distilled off under reduced pressure. The obtained residue was dissolved in developing solvent (benzene: ethyl acetate=85:15) and purified by silica gel column chromatography. The solution secondly eluted was collected and the solvent was distilled off therefrom to give the desired product (VI-4) as white solid (403 mg, yield 57.4%, mp 80°–83° C.).

In a manner similar to that described above, 1(3-chloropropyl)-4-phenyl-2(1H)-quinolinone (VI-5), 4-(4-chlorophenyl)-1-(3-chloropropyl)-2(1H)-quinolinone (VI-6) and 1-(3-chloropropyl)-4-(4-methylphenyl)-2(1H)-quinolinone (VI-7) were prepared.

The compound 1-(3-chloropropyl)-4-phenyl-2(1H)-quinolinone (VI-5) is known from JP-A-49359/1981.

Example 7 (method B2)

Preparation of 1-[3-[4-(1H-indol-3-yl)-piperidinyl]propyl]-6-chloro-2-(1H)-quinolinone (VII-1)

A suspension of 1-(3-chloropropyl)-6-chloro- 2(1H)-quinolinone (VI-1) (540 mg, 2.11 mmol), 3-(4-piperidinyl)- 1H-indole (464 mg, 2.32 mmol) and sodium hydrogencarbonate (266 mg, 3.17 mmol) in dry dimethylformamide (4 ml) was stirred at 80° C. for 18 hours. The reaction mixture was poured into ice-water, and the separated solid was filtered off by aspiration. The solid was washed, dried and then recrystallized from methanol water to give the desired product (VII-1) (730 mg, yield 82%).

In a manner similar to that described above, 1-[ 3-[4-(1H-indol-3-yl)-1-piperidinyl]propyl]-6-methyl-2(1H)-quinolinone(VII- 2) and 1-[3-[4-(1H-indol-3-yl)-1-piperidinyl] propyl]-2(1H)-quinolinone (VII-3) were prepared.

Example 8 (method B2)

Preparation of 1-[3-[4-(1H-indol-3-yl)-1-piperidinyl]propyl]- 4-methyl-2-(1H)-quinolinone (VII-4)

A suspension of 1-(3-chloropropyl)-4-methyl-2( 1H)-quinolinone (VI-4) (455 mg, 1.93 mmol), 3-(4-piperidinyl)-1H-indole (350 mg, 1.75 mmol) and sodium hydrogencarbonate (220 mg, 2.63 mmol) in dry dimethylformamide 6 ml was allowed to react at 90° C. for 15 hours. Ice-water was poured into the reaction mixture and then the separated solid was filtered off by aspiration. The solid was dissolved in chloroform, then dried and the solvent was distilled off under the reduced pressure. The residue was dissolved in developing solvent (chloroform: methanol=9:1) and purified by silica gel column chromatography. After removing the first eluted impurity, a colorless solution was collected and the solvent was distilled off to give the desired product (VII-4) (450 mg) as a pale yellow solid (yield 64.4%, mp 74°–77° C.).

In a manner similar to that described above, 1-[3-[4-(1H-indol-3-yl)-piperidinyl]propyl]-4-phenyl-2(1H)-quinolinone (VII-5), 4-(4-chlorophenyl)-1-[3-[4-(1H-indol-3-yl)-1-piperidinyl] propyl]-2(1H)-quinolinone (VII-6) and 1-[3-[4-(1H-indol-3-yl)-piperidinyl]propyl]-4-(4-methylphenyl)- 2(1H)-quinolinone (VII-7) were prepared.

Preference Example 12 (method A13)

Preparation of 4-(2-bromoethyl)-3,4-dihydro-2(1H)-quinolinone (II'-1)

A suspension of 3,4-dihydro-4-(2-hydroxyethyl)-2-( 1H)-quinolinone (1.6 g, 8.37 mmol) in 47% aqueous hydrobromic acid (30 ml) was allowed to react at 100° C. for 72 hours. The reaction mixture was poured into ice-water and then extracted with chloroform (300 ml×1). The organic layer was dried (over anhydrous magnesium sulfate) and then the solvent was distilled off. The residue was dissolved in developing solvent (chloroform: methanol=95:5) and purified by silica gel column chromatography. A first eluted colorless solution was collected and the solvent was distilled off to give the entitled compound (II'-1) (1.807 g, yield 85.0%, mp 125°–127° C. (methanol/water)). The starting material 3,4-dihydro-4-(2-hydroxyethyl)-2(1H)-quinolinone was prepared according to Yakugaku Zasshi, 85(10), 871–875(1965).

Example 9 (method A15)

Preparation of 3,4-dihydro-4-[2-[4-(1H-indol-3-yl)-1-piperidinyl] ethyl]-2(1H)-quinolinone (IV-1)

A suspension of 4-(2-bromoethyl)-3,4-dihydro- 2(1H)-quinolinone (II'-1) (500 mg, 1.97 mmol),3-(4-piperidinyl)-1H-indole (394.5 mg, 1.97 mmol) and sodium hydrogencarbonate (248.7 mg, 2.96 mmol) in dry dimethylformamide (5 ml) was allowed to react at 90° C. for 4 hours. Ice-water (50 ml) was poured into the reaction mixture and then the separated solid was filtered by aspiration. The residue was washed with water and dissolved in chloroform (50 ml). The solution was dried (anhydrous magnesium sulfate) and the solvent was distilled off. The residue was dissolved in developing solvent (chloroform: methanol=85:15) and purified by silica gel column chromatography (chloroform: methanol=85:15). After removing the first eluted impurity, a colorless solution was collected and the solvent distilled off to give the desired product (IV-1) (540 mg) as a pale yellow solid (yield 73.4%, mp 115°–117° C. (methanol/tetrahydrofuran/water).

Reference Example 13 Method A17

Preparation of 4-(2-bromoethyl)-6-nitro-2(1H)-quinolinone (II-9)

To a mixture of nitric acid (60%) (21 ml) and concentrated sulfuric acid (14 ml) was added 4-(2-bromoethyl)- 2(1H)-quinolinone (II-2) (3.5 g, 13.9 mmol) under ice-cooling and then the mixture was stirred at 45° C. (bath temperature) for 45 minutes.

The reaction mixture was poured into ice-water (450 ml) and the separated solid was filtered off, washed with water and dried. The solid was recrystallized from ethanol to give the entitled compound (2.6 g) as pale yellow crystals (mp 215°–217° C. (ethanol)). Yield 63.0 %.

Example 10 (method A19)

Preparation of 4-[2-[4-(1H-indol-3-yl)-1-piperidinyl] ethyl] -6-nitro-2(1H)-quinolinone (III-19)

A suspension of 4-(2-bromoethyl)-6-nitro-2(1H)-quinolinone (II-9) (891 mg, 3.0 mmol), 3-(4-piperidinyl)- 1H-indol (600 mg, 3.0 mmol) and sodium hydrogen carbonate (378 mg, 4.5 mmol) in dimethylformamide (9 ml) was stirred at 50° C. for 30 hours. Then the reaction mixture was poured into water. The precipitated solid was filtered, washed with water, dried and recrystallized from a mixed solvent consisting of methanol, tetrahydrofuran and water to give the desired compound (III-19) (640 mg, yield 51.2%) as pale yellow crystals, mp 251°–253° C. (recrystallized from a mixture of methanol, tetrahydrofuran and water).

Example 11 (method A20)

Preparation of 6-amino-4-[2-[4-(1H-indol-3-yl)-1-piperidinyl] ethyl]-2(1H)-quinolinone (III-20)

Into a mixed solvent of tetrahydrofuran (800 ml) and methanol (200 ml) was dissolved 4-[2-[4-(1H-indol-3-yl)-1-piperidinyl]ethyl]-6-nitro-2(1H)-quinolinone (III-19) (6 g, 14.4 mmol) under heating. Paladium on carbon (2.5 g) was added thereto and the mixture was stirred under hydrogen atmosphere at 55° C. for 4 hours. The reaction mixture was filtered at the same temperature and the solvent was distilled off from the filtrate. The residue was dried and then recrystallized from a mixture of methanol, THF and water to give the desired product (III-20) (4.3 g) as pale yellow crystals (mp 214°–216 ° C. (methanol/tetrahydrofuran water)). Yield 77.3 %.

Example 12 (method A21)

Preparation of 6-acetylamino-4-[2-[4-(1H-indol-3-Yl)-1-piperidinyl] ethyl]-2(1H)-quinolinone (III-21)

To a solution of 6-amino-4-[2-[4-(1H-indol-3-yl)- 1-piperidinyl]ethyl]-2(1H)-quinolinone (III-20) (1 g, 2.59 mmol) in dimethylformamide (8 ml) was added triethylamine (0.7 ml, 5 mmol). To the mixture was added dropwise acetyl chloride (0.2 ml, 2.75 mmol) at 0 ° C. and the mixture was stirred at the same temperature for 15 minutes. The reaction mixture was poured into water and the separated solid was filtered off. After washing with water and drying, the solid was recrystallized from a mixture of methanol, tetrahydrofuran and water to give the desired product (III- 21) (900 mg) as pale yellow crystals (yield 81.1%, mp 180°– 183° C. (methanol/tetrahydrofuran/water).

In a manner similar to that described above, 6-n-butyloxalylamino- 4-[2-[4-(1H-indol-3-yl)-1-piperidinyl] ethyl]-2(1H)-quinolinone (III-22) was prepared.

| n | R | R' | R[1] | Yield (%) | Formula (MW) | FAB-MS (m/z) | m.p. (solvent) | State |
|---|---|---|---|---|---|---|---|---|
| 2 | H | H | CH$_3$ | 87.2 | C$_{12}$H$_{13}$NO$_2$ (203.23) | 204 (M + H) | 149–150° C. (chloroform-hexane) | white crystals |
| 2 | 7-Br | H | H | 94.9 | C$_{11}$H$_{10}$BrNO$_2$ (268.11) | 268 (M + H) | 263–265° C. (MeOH-THF-H$_2$O) | white crystals |
| 2 | 6-CH$_3$ | H | " | 79.1 | C$_{12}$H$_{13}$NO$_2$ (203.24) | 204 (M + H) | 243–245° C. (MeOH — H$_2$O) | white crystals |
| 2 | 8-CH3 | H | " | 94.6 | C$_{12}$H$_{13}$NO$_2$ (203.24) | 204 (M + H) | 240–242° C. (MeOH-THF-H$_2$O) | white crystals |
| 2 | 7-CH$_3$ | H | H | 83.6 | C$_{12}$H$_{13}$NO$_2$ (203.24) | 204 (M + H) | 225–228° C. (MeOH) | white crystals |
| 2 | 6-i-Pr | H | " | 60.5 | C$_{14}$H$_{17}$NO$_2$ (231.29) | 232 (M + H) | 183–185° C. (MeOH — H$_2$O) | white crystals |
| 2 | 5-CH$_3$ | 7-CH$_3$ | " | 53.0 | C$_{13}$H$_{15}$NO$_2$ (217.27) | 218 (M + H) | 267–270° C. (MeOH-THF-H$_2$O) | white crystals |
| 2 | 8-i-Pr | H | " | 72.1 | C$_{14}$H$_{17}$NO$_2$ (231.29) | 232 (M + H) | 103–105° C. (EtOH — H$_2$O) | white crystals |

(III)

(desired product)

| Compound No. | n | R | R' | R[1] | Yield (%) | Formula (MW) | FAB-MS (m/z) (M + H) | mp (solvent) | State |
|---|---|---|---|---|---|---|---|---|---|
| III - 1 | 1 | H | H | H | 47.6 | C$_{23}$H$_{23}$N$_3$O (357.45) | 358 | 244–246° C. (MeOH — H$_2$O) | pale yellow crystals |

-continued

| Compound | | | Structure | Yield (%) | Formula (MW) | MS | mp (solvent) | Appearance |
|---|---|---|---|---|---|---|---|---|
| III-2 | 2 | " | " | 45.7(A) 70.9(B) | $C_{24}H_{25}N_3O$ (371.46) | 372 (M+H) | 259–260° C.(A) (MeOH-THF-$H_2$O) 259–259.5° C.(B) (MeOH-THF-$H_2$O) | pale yellow crystals |
| III'-2-a | " | " | hydrochloride | 45.0 | — | — | 290–293° C. (MeOH) | pale yellow crystals |
| III'-2-b | " | " | maleate | 61.4 | — | — | 138–141° C. (Acetone-MeOH) | pale yellow crystals |
| III'-2-c | " | " | fumarate | 82.0 | — | — | 262–264° C. | white solid |
| III-3 | 3 | " | " | 75.9 | $C_{25}H_{27}N_3O$ (385.49) | 386 (M+H) | 204–206° C. (MeOH) | pale yellow crystals |
| III-4 | 4 | " | " | 74.7 | $C_{26}H_{29}N_3O$ (399.49) | 400 (M+H) | 130–132° C. (MeOH—$H_2$O) | pale yellow crystals |
| III-5 | 5 | H | H | 63.7 | $C_{27}H_{31}N_3O$ (413.49) | 414 (M+H) | 187–189° C.(MeOH) | pale yellow crystals |
| III-6 | 1 | " | (Ph-CH(Ph)-N-piperidine structure) | 80.0 | $C_{27}H_{29}N_3O$ (409.53) | 410 (M+H) | 149–151° C.(MeOH—$H_2$O) | white crystals |
| III-7 | 2 | " | " | 45.3 | $C_{28}H_{29}N_3O$ (423.53) | 424 (M+H) | 204–206° C. (MeOH-THF) | white crystals |
| III-8 | 3 | " | " | 60.5 | $C_{29}H_{31}N_3O$ (437.56) | 438 (M+H) | 109–111° C. (benzene-hexane) | white crystals |
| III-9 | 2 | H | (Ph-CH(4-ClC$_6$H$_4$)-N-piperidine) | 38.0 | $C_{28}H_{28}ClN_3O$ (457.58) | 458 (M+H) | 115–117° C. (benzene-hexane) | pale yellow crystals |
| III-10 | 1 | " | (Ph-OCH(Ph)-piperidine) | 60.9 | $C_{28}H_{28}N_2O_2$ (424.52) | 425 (M+H) | 215–216° C.(MeOH-THF-$H_2$O) | white crystals |
| III-11 | 2 | " | " | 44.6 | $C_{29}H_{30}N_2O_2$ (438.57) | 439 (M+H) | 182–184° C. (MeOH-THF-$H_2$O) | white crystals |
| III-12 | 3 | " | " | 74.5 | $C_{30}H_{32}N_2O_2$ (452.60) | 453 (M+H) | 192–193° C. (MeOH-THF-$H_2$O) | white crystals |

-continued

| | | | | | | | | |
|---|---|---|---|---|---|---|---|---|
| III-13 | 1 | H | H | H | (structure: tricyclic ketone with thiophene, piperidine) | 51.9 | $C_{28}H_{24}N_2O_2S$ (452.57)(M+H) | 182–185° C.(EtOH) | pale yellow crystals |
| III-14 | 2 | " | " | " | " | 28.7 | $C_{29}H_{26}N_2O_2S$ (466.60) 467 (M+H) | 188–191° C. (MeOH-THF-$H_2O$) | pale yellow crystals |
| III-15 | 3 | " | " | " | " | 67.3 | $C_{30}H_{28}N_2O_2S$ (480.62) 481 (M+H) | 230–232° C. (MeOH-THF-$H_2O$) | pale yellow crystals |
| III-16 | 1 | " | " | $CH_3$ | (structure: indole-piperidine) | 65.0 | $C_{24}H_{25}N_3O$ (371.47)(M+H) | 228–229° C.(MeOH-THF) | white crystals |
| III-17 | 2 | " | " | " | " | 74.0 | $C_{25}H_{27}N_3O$ (385.49) 386 (M+H) | 79–81° C. (benzene-hexane) | white crystals |
| III-18 | 2 | 7-Br | H | H | (structure: indole-piperidine) | 51.2 | $C_{24}H_{24}BrN_3O$ (450.50)(M+H) | 218–220° C.(MeOH-THF) | pale yellow crystals |
| III-19 | " | 6-$NO_2$ | " | " | " | 51.2 | $C_{24}H_{24}N_4O_3$ (416.48) 417 (M+H) | 251–253° C. (MeOH-THF-$H_2O$) | pale yellow crystals |
| III-20 | " | 6-$NH_2$ | " | " | " | 77.3 | $C_{24}H_{26}N_4O$ (386.50) 387 (M+H) | 214–216° C. (MeOH-THF-$H_2O$) | pale yellow crystals |
| III-21 | " | 6-NHCCH$_3$ (O=) | " | " | " | 81.1 | $C_{26}H_{28}N_4O_2$ (428.529)(M+H) | 180–183° C. (MeOH-THF-$H_2O$) | pale yellow crystals |
| III-22 | " | 6-NHCC—O-nBu (O=, O=) | " | " | " | 60.0 | $C_{30}H_{34}N_4O_4$ (514.62) 515 (M+H) | 237–238° C. (MeOH-THF-$H_2O$) | pale yellow crystals |

-continued (III)

*Yield for III'-2-a - III'-2-c was calculated based on III-2.

| Compound No. | n | R | R' | R¹ | R² | Yield (%) | Formula (MW) | FAB-MS (m/z) | mp (solvent) | State |
|---|---|---|---|---|---|---|---|---|---|---|
| III-23 | 2 | 6-CH₃ | H | H | [indol-3-yl-piperidine structure] | 59.7 | $C_{25}H_{27}N_3O$ (385.51) | 385.5 (M+H) | 255–257° C.(MeOH-THF-H₂O) | white crystals |
| III-24 | " | 8-CH₃ | " | " | " | 67.4 | $C_{25}H_{27}N_3O$ (385.51) | 386 (M+H) | 235.5–238.0° C. (DMF-H₂O) | white crystals |
| III-25 | " | 7-CH₃ | " | " | " | 68.3 | $C_{25}H_{27}N_3O$ (385.51) | 386 (M+H) | 260–262° C. (MeOH-THF-H₂O) | white crystals |
| III-26 | " | 6-i-Pr | " | " | " | 71.6 | $C_{27}H_{31}N_3O$ (413.56) | 414 (M+H) | 272–274° C. (DMF-H₂O) | slightly yellow crystals |
| III-27 | " | 5-CH₃ | 7-CH₃ | " | " | 40.0 | $C_{26}H_{29}N_3O$ (399.54) | 400 (M+H) | 272–273° C. (MeOH-THF-H₂O) | white crystals |
| III-28 | 2 | 8-i-Pr | H | H | [indol-3-yl-piperidine structure] | 69.6 | $C_{27}H_{31}N_3O$ (413.56) | 414 (M+H) | 243–245° C.(MeOH-THF-H₂O) | slightly yellow crystals |

(IV)

(desired product)

-continued

| No. | n | R | R' | R¹ | R² | Yield (%) | Formula (MW) | FAB-MS (m/z) | mp (solvent) | State |
|---|---|---|---|---|---|---|---|---|---|---|
| IV - 1 | 2 | H | H | H | (structure shown) | 73.4 | C₂₄H₂₇N₃O(373.48)374(M + H) | | 115–117° C. MeOH-THF-H₂O) | pale yellow solid |

(VI)

(intermediate)

| No. | n | R | B | Yield (%) | Formula (MW) | FAB-MS (m/z) | mp (solvent) | State |
|---|---|---|---|---|---|---|---|---|
| VI - 1 | 3 | 6-Cl | H | 35 | C₁₂H₁₁Cl₂NO (256.13) | — | 111–112° C. (benzene-hexane) | white crystals |
| VI - 2 | " | 6-CH₃ | " | 45 | C₁₃H₁₄ClNO (235.71) | — | 107–108° C. (benzene-hexane) | white crystals |
| VI - 3 | " | 6-H | " | 39 | C₁₂H₁₂ClNO (221.69) | — | 77–79° C. (benzene-hexane) | white crystals |
| VI - 4 | " | " | CH₃ | 57.4 | C₁₃H₁₄ClNO (235.72) | — | 80–83° C. | white solid |
| *VI - 5 | " | " | C₆H₅ | 55.7 | C₁₈H₁₆ClNO (297.79) | — | 114–115° C. (—) | white solid |
| VI - 6 | 3 | 6-H | 4-ClC₆H₄ | 61.4 | C₁₈H₁₅Cl₂NO (332.23) | 332 (M + H) | 108–109° C. (MeOH—H₂O) | white solid |
| VI - 7 | " | " | 4-CH₃C₆H₄ | 46.9 | C₁₉H₁₈ClNO (311.81) | 312 (M + H) | 103–105° C. (MeOH—H₂O) | white solid |

*Known compound (RN-79145-360-1)

(VII)

(desired product)

| No. | n | R | B | R² | Yield (%) | Formula (MW) | FAB-MS | mp (solvent) | State |
|---|---|---|---|---|---|---|---|---|---|

| | | | | | | |
|---|---|---|---|---|---|---|
| VII - 1 | 3 | 6-Cl | H | 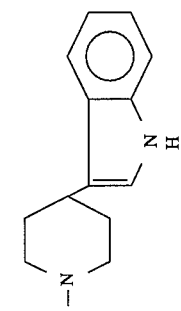 | 82 | $C_{25}H_{26}ClN_3O$ (419.95) 420 (M + H) | 113–114° C. (MeOH—$H_2O$) white crystals |
| VII - 2 | " | 6-$CH_3$ | " | " | 70 | $C_{26}H_{29}N_3O$ (399.53) 400 (M + H) | 140–143° C. (ethyl acetate-hexane) white crystals |
| VII - 3 | " | 6-H | " | " | 81 | $C_{25}H_{27}N_3O$ (385.51) 386 (M + H) | 137–140° C. (ethyl acetate-hexane) white crystals |
| VII - 4 | " | 6-H | $CH_3$ | " | 64.4 | $C_{26}H_{29}N_3O$ (399.54) — | 74–77° C. (—) slightly yellow solid |
| VII - 5 | " | " | $C_6H_5$ | " | 95.0 | $C_{31}H_{31}N_3O$ (461.61) 462 (M + H) | 74–77° C. (chloroform-hexane) white solid |
| VII - 6 | " | 6-H | 4-$ClC_6H_4$ | " | 68.6 | $C_{31}H_{30}ClN_3O$ (496.05) 496 | 169–171° C. white solid |
| VII - 7 | " | " | 4-$CH_3CH_6H_4$ | " | 51.6 | $C_{32}H_{33}ClN_3O$ (475.63) 476 (M + H) | (MeOH—$H_2O$) 162–164° C. (chloroform-petroleum ether) white solid |

| No. | Formula | IR($v^{KBr_{max}}$, cm$^{-1}$) | $^1$H-NMR($\delta$, DMSO-d$_6$, 90MHz) |
|---|---|---|---|
| | 1-methyl-4-(CH$_2$COOH)-quinolin-2(1H)-one | 3300~2100<br>1700<br>1640 | 3.62(s, 3H, —N—CH$_3$)<br>3.87(s, 2H, —CH$_2$—)<br>6.61(s, 1H, quinolinone-H)<br>7.13~7.87(m, 4H, arom-H) |

| No. | Formula | IR($v^{KBr_{max}}$, cm$^{-1}$) | $^1$H-NMR($\delta$, DMSO-d$_6$, 300MHz) |
|---|---|---|---|
| | 4-((CH$_2$)$_3$COOH)-quinolin-2(1H)-one | 3250~2000<br>1700<br>1650 | 1.83(quint., 2H, —CH$_2$—, J=7Hz)<br>2.34(t, 2H, —CH$_2$—, J=7Hz)<br>2.81(t, 2H, —CH$_2$—, J=7Hz)<br>6.34(s, 1H, quinolinone-H)<br>7.19(dt, 1H, arom-H, J=1, 8Hz)<br>7.31(dd, 1H, arom-H, J=1, 8Hz)<br>7.49(dt, 1H, arom-H, J=1, 8Hz)<br>7.80(dd, 1H, arom-H, J=1, 8Hz)<br>11.61(brs., 1H, NH) |
| | 4-((CH$_2$)$_4$COOH)-quinolin-2(1H)-one | 3600~2000<br>1660 | 1.55~1.70(m, 4H, —CH$_2$—×2)<br>2.27(bt., 2H, —CH$_2$COOH)<br>2.81(bt., 2H, —CH$_2$—)<br>6.35(s, 1H, quinolinone-H)<br>7.18(dt, 1H, arom-H, J=1, 8Hz)<br>7.31(dd, 1H, arom-H, J=1, 8Hz)<br>7.48(dd, 1H, arom-H, J=1, 8Hz)<br>7.75(dd, 1H, arom-H, J=1, 8Hz)<br>11.59(brs., 1H, NH) |
| | 4-((CH$_2$)$_3$COOCH$_3$)-quinolin-2(1H)-one | 1730<br>1660 | 1.87(quint., 2H, —CH$_2$—, J=7Hz)<br>2.44(t, 2H, —CH$_2$—, J=7Hz)<br>2.82(t, 2H, —CH$_2$—, J=7Hz)<br>3.60(s, 3H, —COOCH$_3$)<br>6.35(s, 1H, quinolinone-H)<br>7.19(ddd, 1H, arom-H, J=1,7,8Hz)<br>7.31(dd, 1H, arom-H, J=1, 8Hz)<br>7.49(ddd, 1H, arom-H, J=1,7,8Hz)<br>7.79(dd, 1H, arom-H, J=1, 8Hz) |

-continued

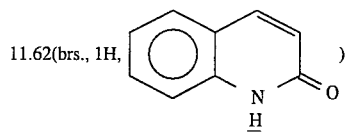
11.62(brs., 1H, )

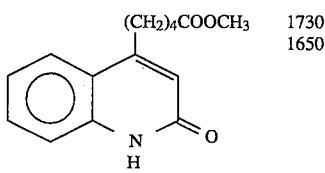
(CH$_2$)$_4$COOCH$_3$ 1730
1650

1.55~1.70(m, 4H, —C$\underline{H}_2$×2)
2.37(bt., 2H, —C$\underline{H}_2$COOCH$_3$)
2.81(bt., 2H, —C$\underline{H}_2$—)
3.58(s, 3H, —COOC$\underline{H}_3$)

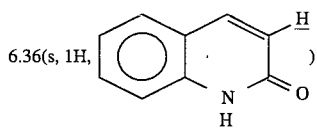
6.36(s, 1H, )

7.18(dt., 1H, arom-$\underline{H}$, J=1, 8Hz)
7.31(dt, 1H, arom-$\underline{H}$, J=1, 8Hz)
7.48(dt, 1H, arom-$\underline{H}$, J=1, 8Hz)
7.75(d, 1H, arom-$\underline{H}$, J=8Hz)

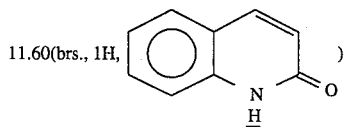
11.60(brs., 1H, )

| No. | Formula | IR($v^{KBr max, cm^{-1}}$) | $^1$H-NMR($\delta$, CDCl$_3$, 90MHz) |
|---|---|---|---|

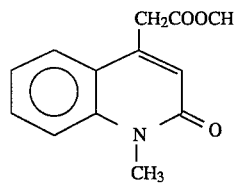

| No. | Formula | IR($v^{KBr max, cm^{-1}}$) | $^1$H-NMR($\delta$, DMSO-d$_6$, 90MHz) |
|---|---|---|---|

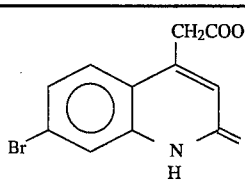

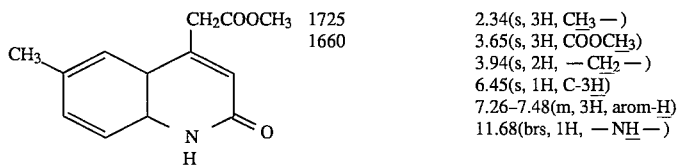

2.34(s, 3H, C$\underline{H}_3$—)
3.65(s, 3H, COOC$\underline{H}_3$)
3.94(s, 2H, —C$\underline{H}_2$—)
6.45(s, 1H, C-3$\underline{H}$)
7.26–7.48(m, 3H, arom-$\underline{H}$)
11.68(brs, 1H, —N$\underline{H}$—)

Known compound JP-A-157267/1990

-continued

| Formula | IR | ¹H-NMR |
|---|---|---|
| 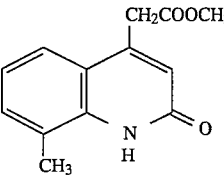 8-CH₃, 4-CH₂COOCH₃ quinolinone | 1730, 1650 | 2.45(s, 3H, CH₃)<br>3.67(s, 3H, COOCH₃)<br>3.98(s, 2H, —CH₂—)<br>6.51(s, 1H, C-3H)<br>6.97–7.53(m, 3H, arom-H)<br>10.81(brs, 1H, —NHCO—) |
| 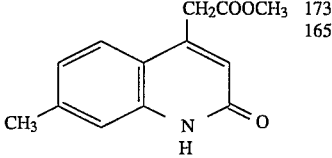 7-CH₃, 4-CH₂COOCH₃ quinolinone | 1730, 1650 | 2.39(s, 3H, CH₃—)<br>3.64(s, 3H, COOCH₃)<br>3.93(s, 2H, —CH₂—)<br>6.44(s, 1H, C-3H)<br>6.85–7.57(m, 3H, arom-H)<br>11.60(brs, 1H, —NHCO—) |
| 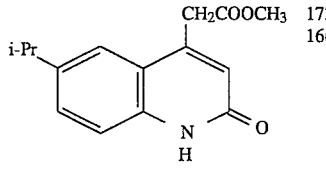 6-i-Pr, 4-CH₂COOCH₃ quinolinone | 1735, 1660 | 1.22(d, 6H, (CH₃)₂CH—)<br>2.69–3.40(m, 1H, (CH₃)₂CH)<br>3.68(s, 3H, COOCH₃)<br>3.93(s, 2H, —CH₂)<br>6.46(s, 1H, C-3H)<br>7.24–7.49(m, 3H, arom-H)<br>11.68(brs, 1H, —NHCO—) |
| 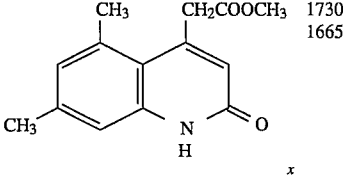 5,7-(CH₃)₂, 4-CH₂COOCH₃ quinolinone | 1730, 1665 | 2.29(s, 3H, CH₃)<br>2.53(s, 3H, CH₃)<br>3.66(s, 3H, COOCH₃)<br>4.09(s, 2H, CH₂)<br>6.35(s, 1H, C-3H)<br>6.79(s, 1H, arom-H)<br>7.01(s, 1H, arom-H)<br>11.58(brs, 1H, —NHCO—) |
| 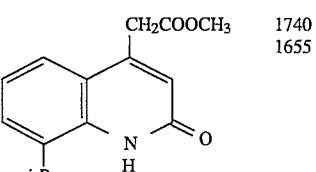 8-i-Pr, 4-CH₂COOCH₃ quinolinone | 1740, 1655 | 1.23(d, 6H, (CH₃)₂CH)<br>2.83–3.40(m, 1H, (CH₃)₂CH)<br>3.70(s, 3H, COOCH₃)<br>3.97(s, 2H, CH₂)<br>6.51(s, 1H, C-3H)<br>7.13–7.53(m, 3H, arom-H)<br>10.98(brs, 1H, NHCO) |

| No. | Formula | IR(υ^KBrmax, cm⁻¹) | ¹H-NMR(δ, DMSO-d₆, 300MHz) |
|---|---|---|---|
| | 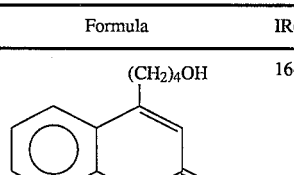 4-(CH₂)₄OH quinolinone | 1640 | 1.48–1.72(m, 4H, —CH₂×2)<br>2.80(t, 2H, —CH₂—J=7Hz)<br>3.39–3.50(m, 2H, —CH₂OH)<br>4.41(t, 1H, —CH₂OH, J=5Hz)<br>6.35(s, 1H, 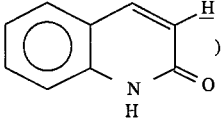)<br>7.18(ddd, 1H, arom-H, J=1, 7, 8Hz)<br>7.31(dd, 1H, arom-H, J=1, 8Hz)<br>7.48(ddd, 1H, arom-H, J=1, 7, 8Hz)<br>7.76(dd, 1H, arom-H, J=1, 8Hz)<br>11.59(brs., 1H, 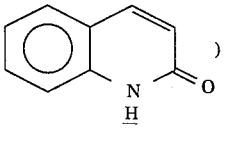) |

| No. | Formula | IR($v^{KBr}_{max}$, cm$^{-1}$) | $^1$H-NMR($\delta$, CDCl$_3$, 90MHz) |
|---|---|---|---|
|  | (structure: 4-(CH$_2$)$_5$OH carbostyril, NH) | 3425<br>1640 | 1.33~1.55(m, 4H, —C$\underline{H}_2$—×2)<br>1.62(quint., 2H, —C$\underline{H}_2$—, J=7Hz)<br>2.79(t, 2H, —C$\underline{H}_2$—, J=7Hz)<br>3.30~3.45(m, 2H, —C$\underline{H}_2$OH)<br>4.36(t, 1H, —CH$_2$O$\underline{H}$, J=5Hz)<br>6.35(s, 1H, 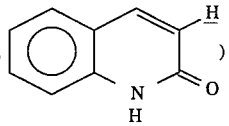)<br>7.18(dt, 1H, arom-$\underline{H}$, J=1, 8Hz)<br>7.31(dd, 1H, arom-$\underline{H}$, J=1, 8Hz)<br>7.48(dt, 1H, arom-$\underline{H}$, J=1, 8Hz)<br>7.74(dd, 1H, arom-$\underline{H}$, J=1, 8Hz)<br>11.59(brs., 1H, 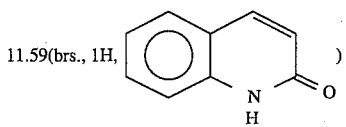) |

| No. | Formula | IR($v^{KBr}_{max}$, cm$^{-1}$) | $^1$H-NMR($\delta$, CDCl$_3$, 90MHz) |
|---|---|---|---|
|  | (structure: 4-CH$_2$CH$_2$OH, N-CH$_3$ carbostyril) | 3350<br>1630 | 3.10(t, 2H, C$\underline{H}_2$CH$_2$OH, J=6Hz)<br>3.68(s, 3H, —N—C$\underline{H}_3$)<br>4.00(b, 2H, —CH$_2$C$\underline{H}_2$OH)<br>6.66(s, 1H ...)<br>7.13~7.90(m, arom-$\underline{H}$) |

| No. | Formula | IR($v^{KBr}_{max}$, cm$^{-1}$) | $^1$H-NMR($\delta$, DMSO-d$_6$, 90MHz) |
|---|---|---|---|
|  | (structure: 7-Br, 4-CH$_2$CH$_2$OH carbostyril, NH) | 3350<br>1670 | 2.92(t, 2H, —C$\underline{H}_2$CH$_2$OH, J=6Hz)<br>3.70(q, 2H, —CH$_2$C$\underline{H}_2$OH, J=6Hz)<br>4.73(t, 1H, —O$\underline{H}$, J=5Hz)<br>6.41(s, 1H, ...)<br>7.32(dd, 1H, arom-$\underline{H}$, J=2Hz, 9Hz)<br>7.49(d, 1H, arom-$\underline{H}$, J=2Hz)<br>7.71(d, 1H, arom-$\underline{H}$, J=9Hz)<br>11.66(brs, 1H, ...) |
|  | (structure: 6-CH$_3$, 4-CH$_2$CH$_2$OH carbostyril, NH) | 1650 | 2.36(s, 3H, C$\underline{H}_3$—)<br>2.93(t, 2H, —C$\underline{H}_2$—, J=7Hz)<br>3.72(t, 2H, —C$\underline{H}_2$—, J=7Hz)<br>6.36(s, 1H, C-3$\underline{H}$)<br>7.25~7.63(m, 3H, arom-$\underline{H}$)<br>11.58(brs, 1H, —N$\underline{H}$—) |

Known compound JP-A-157267/1990

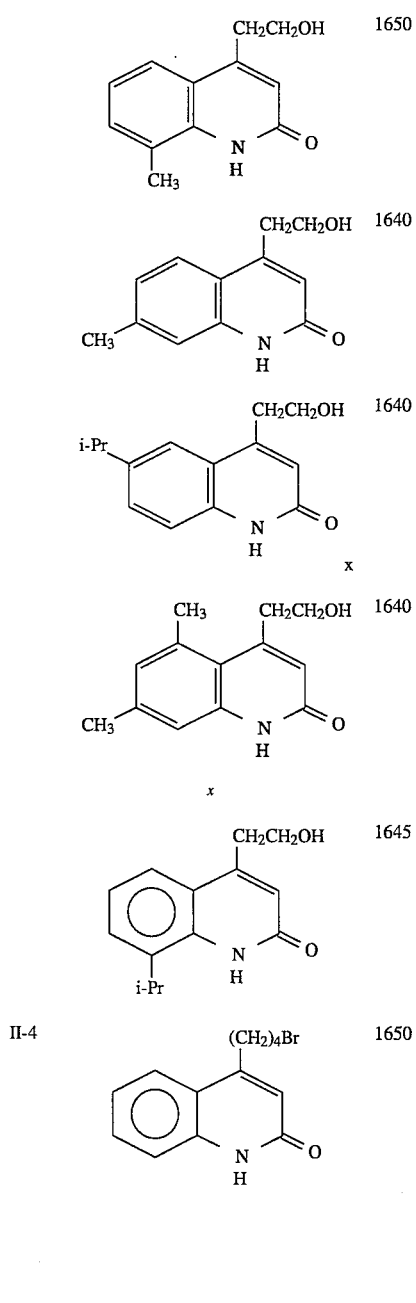

-continued 2.43(s, 3H, C$\underline{H}_3$)
2.95(t, 2H, C$\underline{H}_2$, J=7Hz)
3.69(q, 2H, C$\underline{H}_2$, J=7Hz)
4.72(t, 1H, O$\underline{H}$, J=7Hz)
6.41(s, 1H, C-$\overline{3H}$)
6.96~7.67(m, 3H, arom-$\underline{H}$)
10.63(brs, 1H, —N$\underline{H}$CO—)

2.41(s, 3H, C$\underline{H}_3$—)
2.95(t, 2H, C$\underline{H}_2$, J=7Hz)
3.72(q, 2H, —C$\underline{H}_2$—, J=7Hz)
4.75(t, 1H, O$\underline{H}$, J=7Hz)
6.37(s, 1H, C-$\overline{3H}$)
6.96~7.72(m, 3H, arom-$\underline{H}$)
11.51(brs, 1H, N$\underline{H}$CO)

1.24(d, 6H, (C$\underline{H}_3$)$_2$CH, J=7Hz)
2.72~3.38(m, 1H, (CH$_3$)$_2$C$\underline{H}$—)
2.99(t, 2H, C$\underline{H}_2$, J=7Hz)
3.73(q, 2H, C$\underline{H}_2$, J=7Hz)
4.75(t, 1H, O$\underline{H}$, J=7Hz)
6.37(s, 1H, C-$\overline{3H}$)
7.19~7.56(m, 3H, arom-$\underline{H}$)
11.57(brs, 1H, N$\underline{H}$CO)

2.32(s, 3H, C$\underline{H}_3$)
2.68(s, 3H, C$\underline{H}_3$)
3.16(t, 2H, —C$\underline{H}_2$—, J=7Hz)
3.72(q, 2H, C$\underline{H}_2$, J=7Hz)
4.79(t, 1H, O$\underline{H}$, J=7Hz)
6.32(s, 1H, C-$\overline{3H}$)
6.81(s, 1H, arom-$\underline{H}$)
7.02(s, 1H, arom-$\underline{H}$)
11.40(brs, 1H, —N$\underline{H}$CO—)

1.24(d, 6H, (C$\underline{H}_3$)$_2$CH, J=7Hz)
2.78~3.30(m, 1H, (CH$_3$)$_2$C$\underline{H}$—)
3.01(t, 2H, C$\underline{H}_2$, J=7Hz)
3.78(q, 2H, C$\underline{H}_2$J=7Hz)
4.73(t, 1H, O$\underline{H}$, J=7Hz)
6.48(s, 1H, C-$\overline{3H}$)
7.12~7.70(m, 3H, arom-$\underline{H}$)
11.57(brs, 1H, N$\underline{H}$CO)

1.74(quint., 2H, —C$\underline{H}_2$—, J=7Hz)
1.92(quint., 2H, —C$\underline{H}_2$—, J=7Hz)
2.84(t, 2H, —C$\underline{H}_2$—, J=7Hz)
3.60(t, 2H, —C$\underline{H}_2$Br, J=7Hz)

6.37(s, 1H, 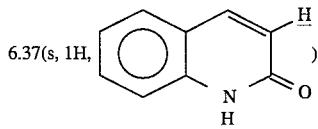 )

7.19(ddd, 1H, arom-$\underline{H}$, J=1, 7, 8Hz)
7.31(dd, 1H, arom-$\underline{H}$, J=1, 8Hz)
7.49(ddd, 1H, arom-$\underline{H}$, J=1, 7, 8Hz)
7.78(dd, 1H, arom-$\underline{H}$, J=1, 8Hz)

11.61(brs., 1H, 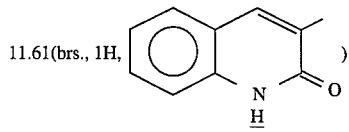 )

| No. | Formula | IR($v^{KBr_{max}}$, cm$^{-1}$) | $^1$H-NMR($\delta$, CDCl$_3$, 90MHz) |
|---|---|---|---|
| II-5 | 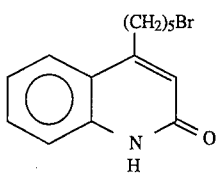 | 1660 | -continued<br>1.50(quint., 2H, —C$\underline{H}_2$—, J=7Hz)<br>1.65(quint., 2H, —C$\underline{H}_2$—, J=7Hz)<br>1.86(quint., 2H, —C$\underline{H}_2$, J=7Hz)<br>2.81(t, 2H, —C$\underline{H}_2$—, J=7Hz)<br>3.54(t, 2H, —C$\underline{H}_2$Br, J=7Hz)<br>6.37(s, 1H, 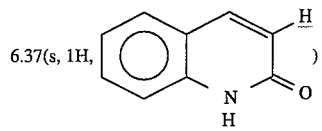)<br>7.19(ddd, 1H, arom-$\underline{H}$, J=1, 7, 8Hz)<br>7.31(dd, 1H, arom-$\underline{H}$, J=1, 8Hz)<br>7.48(ddd, 1H, arom-$\underline{H}$, J=1, 7, 8Hz)<br>7.75(dd, 1H, arom-$\underline{H}$, J=1, 8Hz)<br>11.59(brs., 1H, 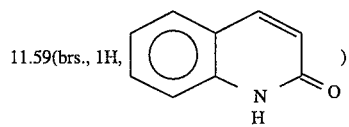) |

| No. | Formula | IR($v^{KBr_{max}}$, cm$^{-1}$) | $^1$H-NMR($\delta$, CDCl$_3$, 90MHz) |
|---|---|---|---|
| II-6 | 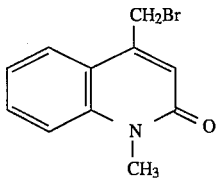 | 1640 | 3.72(s, 3H, N—C$\underline{H}_3$)<br>4.58(s, 2H, —C$\underline{H}_2$—Br)<br>6.81(s, 1H, C-3-olefin-$\underline{H}$)<br>7.25–7.90(m, 4H, arom-$\underline{H}$) |
| II-7 | 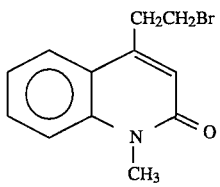 | 1650 | 3.25–3.85(m, 4H, —C$\underline{H}_2$C$\underline{H}_2$—)<br>3.72(s, 3H, —N—C$\underline{H}_3$)<br>6.64(s, 1H, 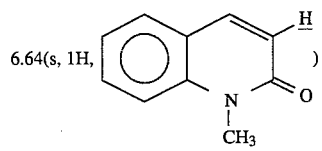)<br>7.18–7.80(m, 4H, arom-$\underline{H}$) |

| No. | Formula | IR($v^{KBr_{max}}$, cm$^{-1}$) | $^1$H-NMR($\delta$, DMSO-d$_6$, 90MHz) |
|---|---|---|---|
| II-8 | 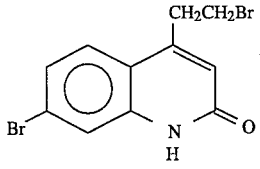 | 1660 | 3.20–3.60(m, 2H, —C$\underline{H}_2$CH$_2$Br)<br>3.81(t, 2H, —CH$_2$C$\underline{H}_2$Br, J=6Hz)<br>6.49(s, 1H, 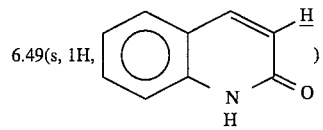)<br>7.33(dd, 1H, arom-$\underline{H}$, J=2Hz, 9Hz)<br>7.51(d, 1H, arom-$\underline{H}$, J=2Hz)<br>7.72(d, 1H, arom-$\underline{H}$, J=9Hz)<br>11.66(brs., 1H, 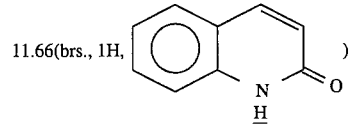) |

| | | | -continued |
|---|---|---|---|
| II-9 | 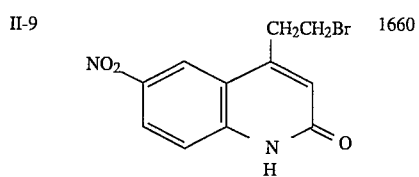 | 1660 | 3.51(t, 2H, CH₂CH₂, J=7Hz)<br>3.91(t, 2H, CH₂Br, J=7Hz)<br>6.64(s, 1H, C-3H)<br>7.47(d, 1H, C-8H, J=9Hz)<br>8.35(dd, 1H, C-7H, J=2, 9Hz)<br>8.58(d, 1H, C-5H, J=2Hz) |
| II-10 | 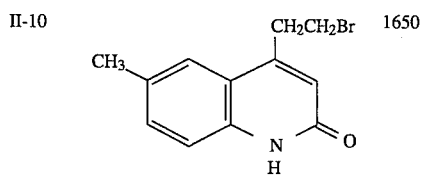 | 1650 | 2.38(s, 3H, CH₃)<br>3.48(t, 2H, CH₂, J=7Hz)<br>3.92(t, 2H, CH₂Br, J=7Hz)<br>6.48(s, 1H, C-3H)<br>7.29~7.73(m, 3H, arom-H)<br>11.60(brs, 1H, NH) |
| II-11 | 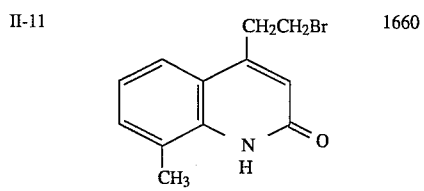 | 1660 | 2.44(s, 3H, CH₃—)<br>3.37(t, 2H, CH₂, J=7Hz)<br>3.85(t, 2H, CH₂, J=7Hz)<br>6.48(s, 1H, C-3H)<br>7.01~7.65(m, 3H, arom-H)<br>10.73(brs, 1H, —NHCO—) |
| II-12 | 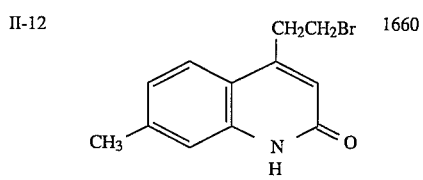 | 1660 | 2.38(s, 3H, CH₃—)<br>3.34(t, 2H, —CH₂—, J=7Hz)<br>3.80(t, 2H, CH₂—, J=7Hz)<br>6.37(s, 1H, C-3H)<br>6.96~7.67(m, 3H, arom-H)<br>11.55(brs, 1H, —NHCO—) |
| II-13 | 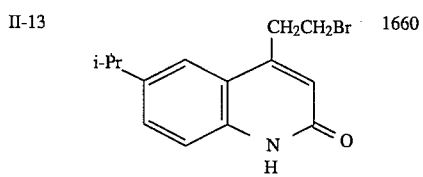 | 1660 | 1.24(d, 6H, (CH₃)₂CH, J=7Hz)<br>2.98(septet, 1H, (CH₃)₂CH, J=7Hz)<br>3.39(t, 2H, CH₂, J=7Hz)<br>3.83(t, 2H, CH₂, J=7Hz)<br>6.44(s, 1H, C-3H)<br>7.22~7.53(m, 3H, arom-H)<br>11.59(brs, 1H, —NHCO—) |
| II-14 | 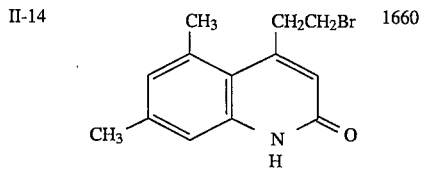 | 1660 | 2.32(s, 3H, CH₃—)<br>2.67(s, 3H, CH₃—)<br>3.36~3.84(m, 4H, CH₂CH₂)<br>6.39(s, 1H, C-3H)<br>6.83(s, 1H, arom-H)<br>7.02(s, 1H, arom-H)<br>11.51(brs, 1H, NHCO) |
| II-15 | 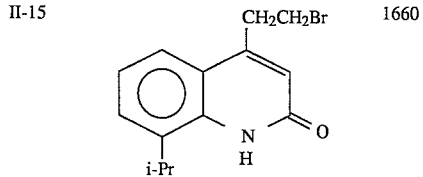 | 1660 | 1.23(d, 6H, (CH₃)₂CH, J=7Hz)<br>2.79~3.38(m, 1H, (CH₃)₂CH)<br>3.42(t, 2H, CH₂, J=7Hz)<br>3.92(t, 2H, CH₂, J=7Hz)<br>6.50(s, 1H, C-3H)<br>7.13~7.70(m, 3H, arom-H)<br>10.70(brs, 1H, NHCO) |
| II'-1 | 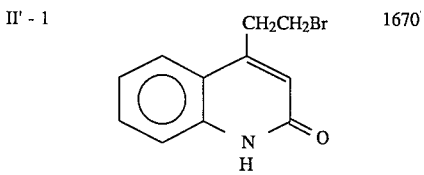 | 1670 | 1.90~2.23(m, 2H, CH₂CH₂Br)<br><br>2.42, 2.60(d, 1H, 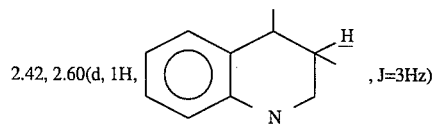, J=3Hz)<br><br>2.77, 2.95(d, 1H, 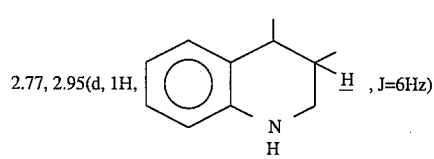, J=6Hz) |

-continued 3.10~3.60(m, 3H, CH2CH2Br, 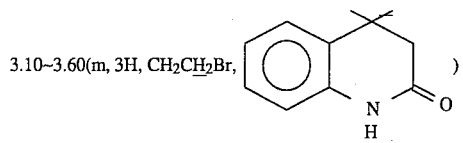)

6.72~7.40(m, 4H, arom-H)

8.20(brs, 1H, 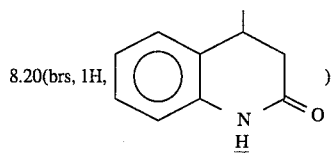)

| No. | IR($v^{KBrmax, cm^{-1}}$) | $^1$H-NMR($\delta$, DMSO-d$_6$, 300MHz) |
|---|---|---|
| III-1 | 1660 | 1.60~1.80(m, 2H, piperidine-H)<br>1.90~2.02(m, 2H, piperidine-H)<br>2.25(t, 2H, piperidine-H, J=11Hz)<br>2.70~2.88(m, 1H, piperidine-H)<br>3.00(d, 2H, piperidine-H, J=12Hz)<br><br>3.72(s, 2H, —CH2—N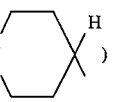)<br><br>6.54(s, 1H, 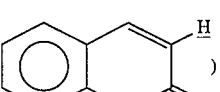)<br><br>6.95(dt, 1H, arom-H, J=1, 8Hz)<br>7.04(dt, 1H, arom-H, J=1, 8Hz)<br><br>7.10(d, 1H, H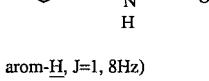, J=2Hz)<br><br>7.19(dt, 1H, arom-H, J=1, 8Hz)<br>7.32(d, 2H, arom-H, J=8Hz)<br>7.49(dt, 1H, arom-H, J=1, 8Hz)<br>7.54(d, 1H, arom-H, J=8Hz)<br>7.95(d, 1H, arom-H, J=8Hz)<br><br>10.75(bs., 1H, 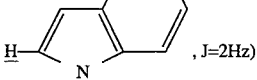)<br><br>11.66(brs., 1H, 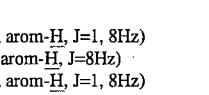) |
| III-2 | 32751640 | 1.60~1.80(m, 2H, piperidine-H)<br>1.90~2.02(m, 2H, piperidine-H)<br>2.19(t, 2H, piperidine-H, J=11Hz)<br><br>2.65(t, 2H, —CH2CH2—N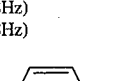, J=8Hz) |

| | | -continued |
|---|---|---|
| III'-2-a | | 2.40~2.70(m, 1H, piperidine-H) |
| | 3350~2000 1650 | 3.01(t, 2H, —CH₂CH₂—N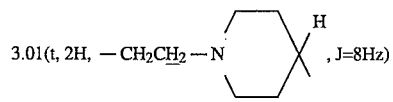, J=8Hz) |
| | | 3.08(d, 2H, piperidine-H, J=11Hz) |
| | | 6.45(s, 1H, 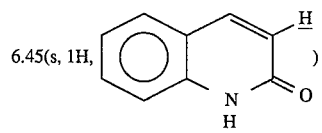) |
| | | 6.95(t, 1H, arom-H, J=8Hz) |
| III'-2-b | | 7.05(t, 1H, arom-H, J=8Hz) |
| | 3700~2100 1750 1660 | 7.09(d, 1H, H—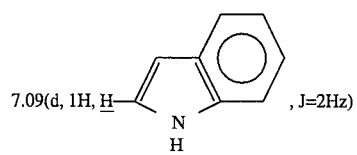, J=2Hz) |
| | | 7.21(t, 1H, arom-H, J=8Hz) |
| | | 7.33(d, 2H, arom-H, J=8Hz) |
| | | 7.50(d, 1H, arom-H, J=8Hz) |
| III'-2-c | | 7.52(d, 1H, arom-H, J=8Hz) |
| | 1675 | 7.78(d, 1H, arom-H, J=8Hz) |
| | | 10.76(brs., 1H, 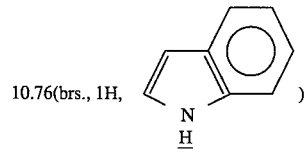) |
| | | 11.62(brs., 1H, 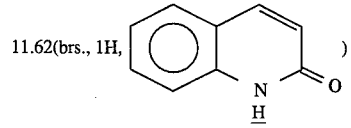) |
| III-3 | 1660 | 1.60~2.00(m, 6H, piperidine-H, —CH₂CH₂CH₂—) |
| | | 2.06(t, 2H, piperidine-H, J=11Hz) |
| | | 2.41(t, 2H, —CH₂CH₂CH₂—N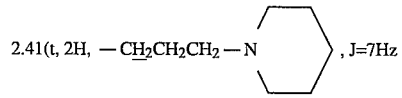, J=7Hz) |
| | | 2.68~2.82(m, 1H, piperidine-H) |
| | | 2.85(t, 2H, —CH₂CH₂CH₂—N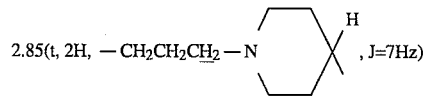, J=7Hz) |
| | | 2.96(d, 2H, piperidine-H, J=11Hz) |

6.39(s, 1H, 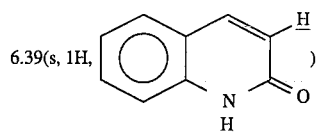 )
6.94(dt, 1H, arom-H, J=1, 8Hz)
7.04(dt, 1H, arom-H, J=1, 8Hz)
7.08(d, 1H, 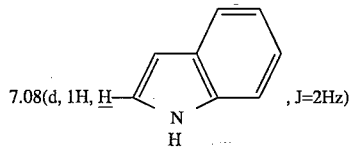, J=2Hz)
7.19(dt, 1H, arom-H, J=1, 8Hz)
7.32(d, 2H, arom-H, J=8Hz)
7.48(dt, 1H, arom-H, J=1, 8Hz)
7.52(t, 1H, arom-H, J=8Hz)
7.80(d, 1H, arom-H, J=8Hz)
10.75(brs., 1H, 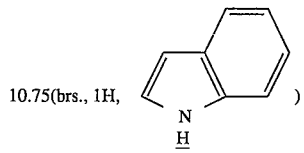 )
11.60(brs., 1H, 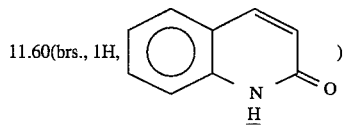 )
| III-4 | 3275 | 1.50~1.78(m, 6H, piperidine-H, —CH₂CH₂CH₂CH₂—) |
| | 1650 | |
2.37(t, 2H, 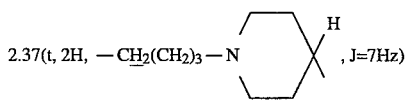, J=7Hz)
2.67~2.85(m, 1H, piperidine-H)
2.83(t, 2H, 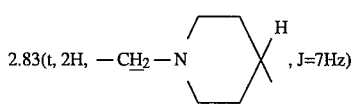, J=7Hz)
2.95(d, 2H, piperidine-H, J=11Hz)
6.37(s, 1H, 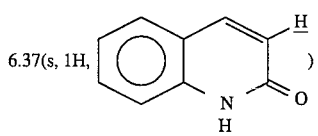 )
6.94(t, 1H, arom-H, J=8Hz)
7.04(t, 1H, arom-H, J=8Hz)
7.07(d, 1H, 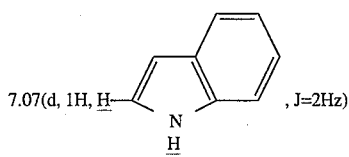, J=2Hz)

-continued
7.20(t, 1H, arom-H, J=8Hz)
7.29~7.38(m, 2H, arom-H)
7.48(t, 1H, arom-H, J=8Hz)
7.51(t, 1H, arom-H, J=8Hz)
7.84(d, 1H, arom-H, J=8Hz)
10.75(brs., 1H, 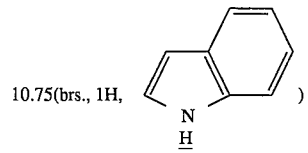 )
11.60(brs., 1H, 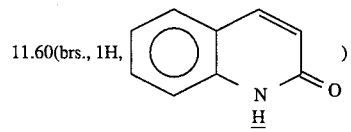 )
| III-5 | 3275 |
|  | 1650 |
1.35~1.75(m, 8H, piperidine-H, —CH2CH2CH2CH2CH2—)
1.85~1.96(m, 2H, piperidine-H)
2.03(t, 2H, piperidine-H, J=11Hz)
2.32(t, 2H, —CH2(CH2)4—N 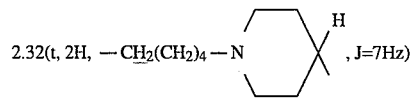, J=7Hz)
2.65~2.90(m, 1H, piperidine-H)
2.81(t, 2H, —CH2—N 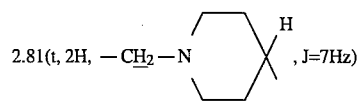, J=7Hz)
2.9(d, 2H, piperidine-H, J=11Hz)
6.37(s, 1H, 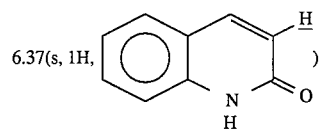 )
6.94(dt, 1H, arom-H, J=1, 8Hz)
7.04(dt, 1H, arom-H, J=1, 8Hz)
7.07(d, 1H, H— 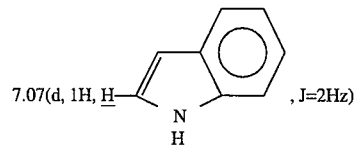, J=2Hz)
7.19(dt, 1H, arom-H, J=1, 8Hz)
7.28~7.36(m, 2H, arom-H)
7.48(dt, 1H arom-H, J=1, 8Hz)
7.51(t, 1H, arom-H, J=8Hz)
7.76(dd, 1H, arom-H, J=1, 8Hz)
10.74(brs., 1H, 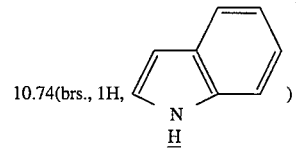 )
11.60(brs., 1H, 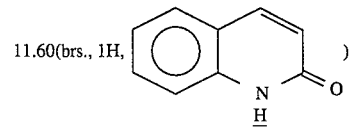 )

III-6
-continued
2.20~2.65(m, 8H, piperazine-H)
3.66(s, 2H, —C$\underline{H}_2$—)

4.29(s, 1H, 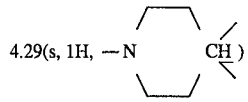)

6.47(s, 1H, 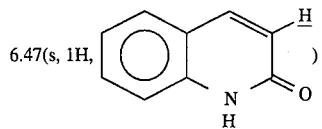)

7.13~7.21(m, 3H, arom-$\underline{H}$)
7.24~7.34(m, 5H, arom-$\underline{H}$)
7.38~7.50(m, 5H, arom-$\underline{H}$)
7.87(d, 1H, arom-$\underline{H}$, J=8Hz)

11.62(brs., 1H, 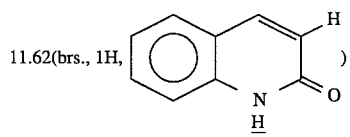)

III-7    1660

2.10~2.70(m, 10H, piperazine-$\underline{H}$, —C$\underline{H}_2$C$\underline{H}_2$—N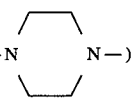N—)

2.95(bt., 2H, —CH$_2$C$\underline{H}_2$—N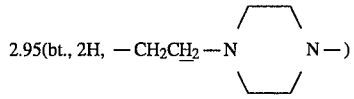N—)

4.28(s, 1H, 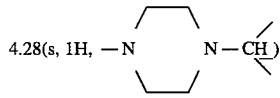)

6.40(s, 1H, 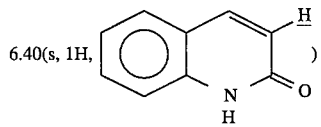)

7.18(t, 3H, arom-$\underline{H}$, J=7Hz)
7.29(t, 5H, arom-$\underline{H}$, J=8Hz)
7.49~7.52(m, 5H, arom-$\underline{H}$)
7.73(d, 1H, arom-$\underline{H}$, J=7Hz)

11.60(brs., 1H, 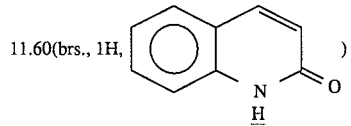)

| No. | IR($\upsilon^{KBr}_{max}$, cm$^{-1}$) | $^1$H-NMR($\delta$, CDCl$_3$, 300MHz) |
|---|---|---|
| III-8 | 1660 | 1.90(quint., 2H, —C$\underline{H}_2$—, J=8Hz)<br>2.30~2.60(m, 10H, piperazine-H, —C$\underline{H}_2$—)<br><br>2.90(t, 2H, —C$\underline{H}_2$—N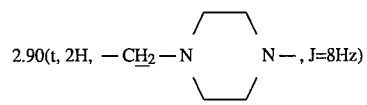N—, J=8Hz) |

-continued 4.23(s, 1H, 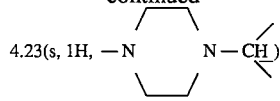)

6.59(s, 1H, 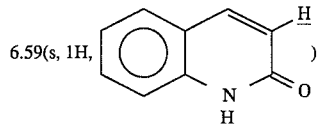)

7.14~7.46(m, 12H, arom-H̲)
7.49(ddd, 1H, arom-H̲, J=1, 7, 8Hz)
7.74(d, 1H, arom-H̲, J=7Hz)

12.08(brs., 1H, 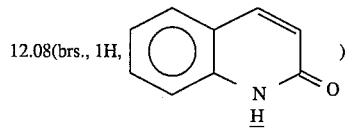)

| No. | IR($\nu^{KBr}_{max}$, cm$^{-1}$) | $^1$H-NMR($\delta$, CDCl$_3$, 200MHz) |
|---|---|---|
| III-9 | 1650 | 2.30~2.70(m, 8H, piperazine-H) |

2.73(t, 2H, 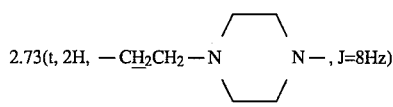, J=8Hz)

3.05(t, 2H, 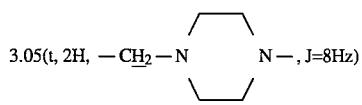, J=8Hz)

4.24(s, 1H, 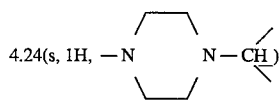)

6.61(s, 1H, 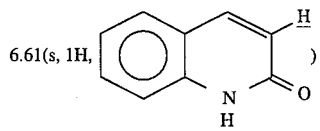)

7.16~7.44(m, 11H, arom-H̲)
7.50(ddd, 1H, arom-H̲, J=1, 7, 8Hz)
7.73(d, 1H, arom-H̲, J=8Hz)

11.51(brs., 1H, 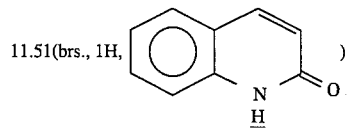)

| No. | IR($\nu^{KBr}_{max}$, cm$^{-1}$) | $^1$H-NMR($\delta$, CDCl$_3$, 200MHz) |
|---|---|---|
| III-10 | 1660 | 1.78~3.50(m, 9H, piperidine-H̲)<br>3.68(s, 2H, —CH̲$_2$—) |

5.51(s, 1H, 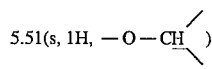)

6.78(s, 1H, C-3-olefin-H̲)
7.16~7.50(m, 13H, arom-H̲)
7.94(d, 1H, arom-H̲, J=9Hz)
11.33(brs, 1H, —NH̲—)

| | | |
|---|---|---|
| III-11 | 1660 | 1.62–3.52(m, 13H, piperidine-H̲—CH$_2$—CH$_2$—) |

5.52(s, 1H, 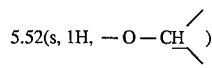)

| No. | IR($v^{KBr}_{max}$, cm$^{-1}$) | $^1$H-NMR($\delta$, CDCl$_3$, 90MHz) |
|---|---|---|
| III-12 | 1660 | 6.58(s, 1H, C-3-olefin-H)<br>7.20–7.50(m, 13H, arom-H)<br>7.76(d, 1H, arom-H, J=8Hz)<br>11.61(brs, 1H, —NH—)<br>1.69–3.48(m, 15H, piperidine-H —CH$_2$CH$_2$CH$_2$—)<br>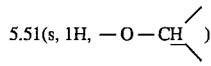<br>5.51(s, 1H, —O—CH)<br>6.57(s, 1H, C-3-olefin-H)<br>7.19–7.49(m, 13H, arom-H)<br>7.75(d, 1H, arom-H, J=8Hz)<br>11.66(brs, 1H, —NH—) |
| III-13 | 1665 | 2.18–2.93(m, 8H, piperidine-H)<br>3.76(s, 2H, —CH$_2$—)<br>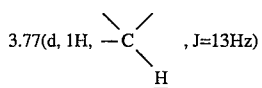<br>3.77(d, 1H, —C—H, J=13Hz)<br>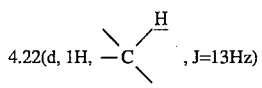<br>4.22(d, 1H, —C—H, J=13Hz)<br>6.85(s, 1H, C-3-olefin-H)<br>7.01–7.56(m, 9H, arom-H)<br>7.95(d, 1H, arom-H, J=8Hz)<br>11.42(brs, 1H, NH) |
| III-14 | 1660 | 2.13–3.11(m, 12H, piperidine-H —CH$_2$CH$_2$—)<br>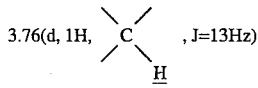<br>3.76(d, 1H, C—H, J=13Hz)<br>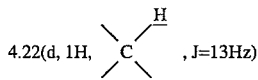<br>4.22(d, 1H, C—H, J=13Hz)<br>6.61(s, 1H, C-3-olefin-H)<br>7.03–7.56(m, 9H, arom-H)<br>7.74(d, 1H, arom-H, J=9Hz)<br>11.68(brs, 1H, —NH—) |
| III-15 | 1660 | 1.84–2.96(m, 14H, piperidne-H —CH$_2$CH$_2$CH$_2$—)<br>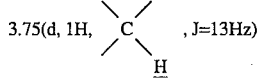<br>3.75(d, 1H, C—H, J=13Hz)<br>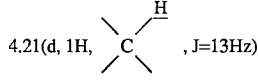<br>4.21(d, 1H, C—H, J=13Hz)<br>6.60(s, 1H, C-3-olefin-H)<br>7.02–7.54(m, 9H, arom-H)<br>7.75(d, 1H, arom-H, J=9Hz)<br>12.18(brs, 1H, —NH—) |

| | -continued | |
|---|---|---|
| III-16 | 1655 | 1.83–3.01(m, 9H, piperidine-H)<br>3.69(s, 5H, N—CH₃, —CH₂—)<br>6.81(s, 1H, C-3-olefin-H)<br>6.92–8.07(m, 10H, arom-H, indole-H) |
| III-17 | 1640 | 1.60–2.50(m, 6H, piperidine-H)<br>2.60–3.30(m, 7H, piperdine-H, CH₂CH₂)<br>3.72(s, 3H, —N—CH₃)<br>6.67(s, 1H, 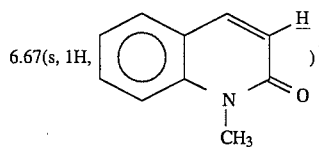 )<br>6.90–7.90(m, 9H, arom-H, indole-H)<br>8.05(brs, 1H, indole-NH) |

| No. | IR($v^{KBr}_{max}$, cm⁻¹) | ¹H-NMR(δ, DMSO-d₆, 90MHz) |
|---|---|---|
| III-18 | 1650 | 1.50–7.35(m, 13H, —CH₂CH₂—, piperidine-H)<br>6.49(s, 1H, 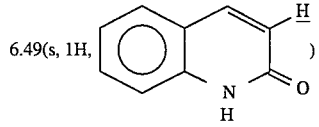 )<br>6.80–7.80(m, 8H, arom-H, indole-H)<br>10.75(bs, 1H, indole-NH)<br>11.68(brs., 1H, 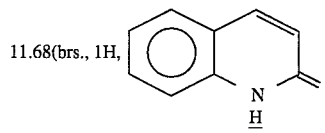 ) |
| III-19 | 1660 | 1.45–3.80(m, 13H, piperidine-H, CH₂CH₂)<br>6.60(s, 1H, C-3 H)<br>6.80–7.60(m, 6H, arom-H)<br>8.30–8.70(m, 2H, arom-H)<br>10.74(brs, 1H, indole-NH)<br>12.10(brs, 1H, NHCO—) |
| III-20 | 1650 | 1.48–3.57(m, 13H, piperidine-H, CH₂CH₂)<br>4.97(brs, 2H, NH₂—)<br>6.38(s, 1H, C-3 H)<br>6.83–7.67(m, 8H, arom-H)<br>10.73(brs, 1H, indole-NH)<br>11.26(brs, 1H, NHCO) |
| III-21 | 1650<br>1660 | 2.06(s, 3H, CH₃CO)<br>1.55–3.83(m, 13H, piperidine-H, CH₂CH₂—)<br>6.43(s, 1H, C-3H)<br>6.87–8.10(m, 8H, arom-H)<br>9.99(s, 1H, CH₃CONH)<br>10.72(s, 1H, indole-NH)<br>11.54(s, 1H, NHCO—) |
| III-22 | 1650<br>1680<br>1715 | 0.97(t, 3H, CH₃—)<br>1.14–3.51(m, 17H, piperidine-H, —CH₂—)<br>4.25(t, 2H, —CH₂O—)<br>6.47(s, 1H, C-3 H)<br>6.86–8.42(m, 8H, arom-H)<br>10.73(brs, 1H, indole-NH)<br>10.84(brs, 1H, —COCONH—)<br>11.66(brs, 1H, —NHCO—) |
| III-23 | 1650 | 1.45–3.78(m, 13H, piperidine-H, —CH₂—)<br>2.40(s, 3H, CH₃—)<br>6.49(s, 1H, C-3H)<br>6.83–7.64(m, 8H, arom-H)<br>10.73(brs, 1H, indole-NH)<br>11.54(brs, 1H, —NH) |

| No. | IR($v^{KBr}_{max}$, cm$^{-1}$) | $^1$H-NMR($\delta$, CDCl$_3$, 90MHz) |
|---|---|---|
| III-24 | 1640 | 2.44(s, 3H, C$\underline{H}_3$—)<br>1.50~3.28(m, 13H, piperidine-$\underline{H}$, C$\underline{H}_2$C$\underline{H}_2$)<br>6.46(s, 1H, C-3$\underline{H}$)<br>6.82~7.68(m, 8H, arom-$\underline{H}$)<br>10.65(brs, 1H, indole-N$\underline{H}$)<br>10.70(brs, 1H, N$\underline{H}$CO) |
| III-25 | 1640 | 2.39(s, 3H, C$\underline{H}_3$—)<br>1.55~3.38(m, 13H, piperidine-$\underline{H}$, —C$\underline{H}_2$C$\underline{H}_2$—)<br>6.40(s, 1H, C-3$\underline{H}$)<br>6.83~7.72(m, 8H, arom-$\underline{H}$)<br>10.71(brs, 1H, indole-N$\underline{H}$)<br>11.48(brs, 1H, —N$\underline{H}$CO—) |
| III-26 | 1650 | 1.26(s, 6H, (C$\underline{H}_3$)$_2$CH—)<br>1.30~3.38(m, 14H, piperidine-$\underline{H}$, —C$\underline{H}_2$C$\underline{H}_2$—, \>C$\underline{H}$—)<br>6.42(s, 1H, C-3$\underline{H}$)<br>6.83~7.57(m, 8H, arom-$\underline{H}$)<br>10.71(brs, 1H, indole-N$\underline{H}$)<br>11.49(brs, 1H, —N$\underline{H}$CO—) |
| III-27 | 1640 | 2.30(s, 3H, C$\underline{H}_3$)<br>2.53(s, 3H, C$\underline{H}_3$)<br>1.50~3.28(m, 13H, piperidine-$\underline{H}$, —C$\underline{H}_2$C$\underline{H}_2$—)<br>6.32(s, 1H, C-3$\underline{H}$)<br>6.81~7.59(m, 7H, arom-$\underline{H}$)<br>10.69(brs, 1H, indole-N$\underline{H}$)<br>11.46(brs, 1H, —N$\underline{H}$CO—) |
| III-28 | 1650 | 1.22(d, 6H, (C$\underline{H}_3$)$_2$CH, J=7Hz)<br>1.56~3.68(m, 14H, piperidine-$\underline{H}$, C$\underline{H}_2$C$\underline{H}_2$—, (C$\underline{H}_3$)$_2$CH)<br>6.46(s, 1H, C-3$\underline{H}$)<br>6.94~7.70(m, 8H, arom-$\underline{H}$)<br>10.69(brs, 2H, N$\underline{H}$CO, indole-N$\underline{H}$) |

| No. | IR($v^{KBr}_{max}$, cm$^{-1}$) | $^1$H-NMR($\delta$, CDCl$_3$, 90MHz) |
|---|---|---|
| IV-1 | 1670 | 1.60~3.30(m, 16H, piperidine-$\underline{H}$, —C$\underline{H}_2$C$\underline{H}_2$—, 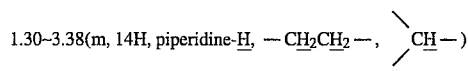)<br>6.60~7.42(m, 8H, arom-$\underline{H}$, indole-$\underline{H}$)<br>7.50~7.72(m, 1H, arom-$\underline{H}$)<br>7.78~8.02(m, 2H, 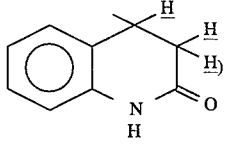, indole-N$\underline{H}$) |
| VI-1 | 1660 | 2.22(q, 2H, —C$\underline{H}_2$—, J=7Hz)<br>3.72(t, 2H, —C$\underline{H}_2$—, J=7Hz)<br>4.43(t, 2H, —C$\underline{H}_2$—, J=7Hz)<br>6.77(d, 1H, C-3-olefin-$\underline{H}$, J=10Hz)<br>7.26~7.65(m, 4H, arom-$\underline{H}$) |
| VI-2 | 1660 | 2.31(q, 2H, —C$\underline{H}_2$—, J=7Hz)<br>2.48(s, 3H, C$\underline{H}_3$—)<br>3.72(t, 2H, —C$\underline{H}_2$—, J=7Hz)<br>4.45(t, 2H, —C$\underline{H}_2$—, J=7Hz)<br>6.64(d, 1H, C-3-olefin-$\underline{H}$, J=10Hz)<br>7.13~7.28(m, 3H, arom-$\underline{H}$)<br>7.62(d, 1H, C-4-olefin-$\underline{H}$, J=10Hz) |
| VI-3 | 1650 | 2.21(q, 2H, —C$\underline{H}_2$—, J=7Hz)<br>3.68(t, 2H, —C$\underline{H}_2$—, J=7Hz)<br>4.46(t, 2H, —C$\underline{H}_2$—, J=7Hz)<br>6.70(d, 1H, C-3-olefin-$\underline{H}$, J=10Hz)<br>7.15~7.74(m, 5H, arom-$\underline{H}$) |

-continued

| No. | IR($v^{KBrmax}$, cm$^{-1}$) | $^1$H-NMR($\delta$, CDCl$_3$, 200MHz) |
|---|---|---|
| VI-4 | 1660<br>1595 | 2.12(tt, 2H, —C$\underline{H}_2$—)<br>2.43(s, 3H, —C$\underline{H}_3$)<br>2.68(t, 2H, —C$\underline{H}_2$—)<br>4.43(t, 2H, —C$\underline{H}_2$—)<br>6.59(s, 1H, position3-$\underline{H}$)<br>7.03~7.98(m, 4H, arom-$\underline{H}$) |
| VI-5 | 1650<br>1585 | 2.34(tt, 2H, —C$\underline{H}_2$—)<br>3.60(t, 1H, —C$\underline{H}_2$—)<br>3.75(t, 1H, —C$\underline{H}_2$—)<br>4.53(t, 2H, —C$\underline{H}_2$—)<br>6.66(s, 1H, position3-$\underline{H}$)<br>7.00~7.75(m, 9H, arom-$\underline{H}$) |

| No. | IR($v^{KBrmax}$, cm$^{-1}$) | $^1$H-NMR($\delta$, CDCl$_3$, 200MHz) |
|---|---|---|
| VI-6 | 1650<br>1585 | 2.28(tt, 2H, —C$\underline{H}_2$—, J=6.4Hz)<br>3.75(t, 2H, —C$\underline{H}_2$)—, J=6.4Hz)<br>4.51(m, 2H, —C$\underline{H}_2$—)<br>6.64(s, 1H, position 3-$\underline{H}$)<br>7.14~7.68(m, 8H, arom-$\underline{H}$) |
| VI-7 | 2950<br>1650<br>1590 | 2.45(s, 3H, C$\underline{H}_3$)<br>2.22–2.43(m, 2H, —C$\underline{H}_2$—)<br>3.75(t, 2H, —C$\underline{H}_2$—, J=6.4Hz)<br>4.52(m, 2H, —C$\underline{H}_2$—)<br>6.65(s, 1H, position 3-$\underline{H}$)<br>7.12~7.66(m, 8H, arom-$\underline{H}$) |
| VII-1 | 1645 | 1.85~3.15(m, 13H, piperidine-$\underline{H}$ —CH$_2$CH$_2$C$\underline{H}_2$—N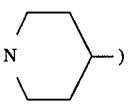)<br>4.37(t, 2H, N—C$\underline{H}_2$—, J=7Hz)<br>6.73(d, 1H, C-3-olefin-$\underline{H}$, J=10Hz)<br>6.99–7.67(m, 9H, arom-$\underline{H}$)<br>8.02(brs, 1H, 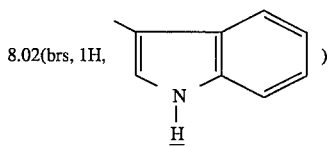) |
| VII-2 | 1645 | 2.40(s, 3H, C$\underline{H}_3$—)<br>1.83–3.19(m, 13H, piperidine-$\underline{H}$ —C$\underline{H}_2$C$\underline{H}_2$—N)<br>4.38(t, 2H, —C$\underline{H}_2$—, J=7Hz)<br>6.65(d, 1H, C-3-olefin-$\underline{H}$, J=9Hz)<br>6.99–7.67(m, 9H, arom-$\underline{H}$)<br>8.06(brs, 1H, 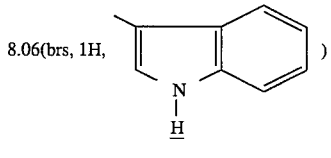) |
| VII-3 | 1640 | 1.86~3.10(m, 13H, piperidine-$\underline{H}$ —CH$_2$CH$_2$C$\underline{H}_2$—N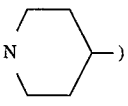)<br>4.40(t, 2H, N—C=O 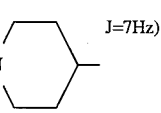 J=7Hz)<br>     $|$<br>     C$\underline{H}_2$CH$_2$CH$_2$—N<br>6.71(d, 1H, C-3 olefin-$\underline{H}$, J=10Hz)<br>6.98–7.70(m, 10H, arom-$\underline{H}$) |

8.19(brs, 1H, 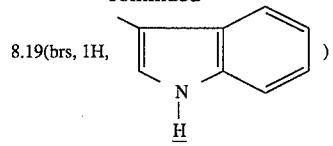 )

| No. | IR($v^{KBrmax}$, cm$^{-1}$) | $^1$H-NMR($\delta$, CDCl$_3$, 300MHz) |
|---|---|---|
| VII-4 | 1650 | 1.78~2.26(m, 8H, piperidine-$\underline{H}$)<br>2.47(d, 3H, —C$\underline{H}_3$, J=1.2Hz)<br>2.57(t, 2H, —C$\underline{H}_2$—, J=6.9Hz)<br>2.81~2.93(m, 1H, piperidine-C$\underline{H}$—)<br>3.05~3.15(m, 2H, —C$\underline{H}_2$—)<br>4.40(t, 2H, —C$\underline{H}_2$—, J=7.1Hz)<br>6.60(d, 1H, position 4-H, J=1.2Hz)<br>6.99(d, 1H, indole position 2, J=1.7Hz)<br>7.07~7.75(m, 8H, arom-$\underline{H}$)<br>8.08(brs, 1H, —N$\underline{H}$—) |

| No. | IR($v^{KBrmax}$, cm$^{-1}$) | $^1$H-NMR($\delta$, CDCl$_3$, 200MHz) |
|---|---|---|
| VII-5 | 1640 | 1.60~2.33(m, 8H, piperidine-$\underline{H}$)<br>2.63(t, 2H, —C$\underline{H}_2$)<br>2.78~3.00(m, 1H, piperidine-C$\underline{H}$—)<br>3.07~3.23(m, 2H, —C$\underline{H}_2$—)<br>4.46(t, 2H, —C$\underline{H}_2$—, J=7.3Hz)<br>6.67(s, 1H, position 4-$\underline{H}$)<br>6.99(d, 1H, indole position 2, J=2.4Hz)<br>7.05~7.69(m, 13H, arom-$\underline{H}$)<br>8.07(brs, 1H, —N$\underline{H}$—) |
| VII-6 | 1640 | 1.68~2.30(m, 8H, piperidine-$\underline{H}$)<br>2.61(t, 2H, —C$\underline{H}_2$—, J=7.1Hz)<br>2.75~2.90(m, 1H, piperidine-C$\underline{H}$—)<br>3.02~3.18(m, 2H, —C$\underline{H}_2$—)<br>4.45(t, 2H, —C$\underline{H}_2$—, J=7.3Hz)<br>6.64(s, 1H, position 4-$\underline{H}$)<br>6.98(d, 1H, indole position 2, J=2.2Hz)<br>7.03~7.68(m, 12H, arom-$\underline{H}$)<br>8.03(brs, 1H, —N$\underline{H}$—) |
| VII-7 | 1635 | 1.54~2.50(m, 8H, piperidine-$\underline{H}$)<br>2.45(s, 3H, —C$\underline{H}_3$)<br>2.64(t, 2H, —C$\underline{H}_2$—, J=7.4Hz)<br>2.60~2.95(m, 1H, piperidine-C$\underline{H}$—)<br>3.05~3.25(m, 2H, —C$\underline{H}_2$—)<br>4.46(t, 2H, —C$\underline{H}_2$—, J=7.5Hz)<br>6.66(s, 1H, position 4-$\underline{H}$)<br>7.00(d, 1H, indole position 2, J=2.2Hz)<br>7.04~7.70(m, 12H, arom-$\underline{H}$)<br>8.05(brs, 1H, —N$\underline{H}$—) |

The compounds of the present invention were assayed for inhibition of passive cutaneous anaphylaxis (PCA) reaction in rats, inhibition of experimental asthma in rats and acute toxicity in mice by the methods described below. Antiserum was prepared according to the method described in *J. Immunol.*, 106, 1002 (1971). The titer (or highest effective dilution which gave a mean 48 hours PCA response of 5 mm in diameter in a rat) of the antiserum used was 1:200.

Test Example 1 (Inhibition of PCA reaction in rats)

Wistar rats were passively sensitized by intracutaneous injection of 0.05 ml antiserum diluted 75 times with physiological saline at two sheared sites of dorsal skin. After 48 hours, 0.5ml/animal of 1% Evans blue-physiological saline containing 2mg ovalbumin was administered into caudal vein to elicit the reaction. After 30 minutes, rats were sacrificed by decapitative bleeding and the dorsal skin was flayed. Dye stuff exuded at the reaction site was extracted according to the method described in *Microbiol. Immunol.*, 22, 89 (1978). Briefly, two circular pieces of sensitized areas and one circular piece of unsensitized area (as the control) were punched at 1.8 cm diameter. The disks were placed in test tubes and treated overnight with 1 ml 1N-KOH at 37° C. Then 9ml 0.6N-H$_3$PO$_4$/acetone (5/13) was added and the mixture was thoroughly stirred and centrifuged (3000 rpm, 10 minutes). The supernatant was assayed for absorption at 620 nm. The amount of dye stuff was calculated from the standard curve previously prepared with known amounts of Evance blue. The conditions of sensitization and the amount of antigen were based on Nippon Yakurigaku Zasshi (Japanese Journal of Pharmacology), 80, 261 (1982).

Test drugs and Oxatomide as a positive control were administered orally before 1 hour of elicitation through a gastric tube at 1 ml/200g body weight. In the test, groups of 6 to 7 animals and groups of 8 to 9 animals were used for test drugs and control, respectively. The results are shown in Table 1 below.

Test Example 2 (Inhibition of experimental asthma in rats)

Wistar rats were passively sensitized by injection into caudal vein of 2.0ml/animal antiserum. After 24 hours, anaphylactic airway contraction caused by administration of antigen was measured by a modified Konzett and Roessler method. Briefly, the animal was fixed at dorsal position under urethane (1.5 g/kg, i.p.) anesthetization and connected with a respirator (Harvard Model 683, respiratory volume: 3–5 ml/respiration; respiratory rate: 72/minute) via an incised tracheal cannula. A branch of the cannula was connected with a bronchospasm transducer (Ugobasile Model 7020) and the amount of air sent by the respirator but did not enter the respiratory system of the rat and overflowed was recorded (Recticorder, Nipponkoden RJG-4124) on a recording paper via an amplifier (Nipponkoden, AB621G). Oxatomide was administered two hours before the test, which is the optimal conditions according to Nippon Yakurigaku Zasshi (Japanese Journal of Pharmacology), 80, 261 (1982), and the other test drugs were orally administered at a rate of 0.2 ml/100 g body weight one hour before the test using a gastric tube. At the end of measurement, the trachea was blocked with a Kocher clamp and the measured values were expressed in percent taking the value at blockage as the maximum contraction (100%). The results are shown in Table 1.

TABLE 1

| Compound NO. | Inhibition of PCA in rat (%) (p.o.) | | Inhibition of Experimental Asthma in rat (%) (p.o.) | |
| --- | --- | --- | --- | --- |
| | 10 mg/kg | other dosage/kg | 10 mg/kg | other dosage/kg |
| III-1 | 73.1 | 58.8 (3 mg) | 14.56 | 14.3 (30 mg) |
| III-2 | 67.4 | 74.6 (30 mg) | 94.80 | 95.49 (3 mg) |
| | | | | 73.01 (1 mg) |
| | | | | 84.27 (0.3 mg) |
| | | | | 27.46 (0.1 mg) |
| III-3 | 69.1 | 96.1 (30 mg) | 84.98 | 88.71 (3 mg) |
| | | 25.8 (3 mg) | | 25.45 (1 mg) |
| | | 21.3 (1 mg) | | |
| III-4 | 12.8 | | 28.67 | |
| III-5 | 66.5 | | 8.87 | |
| III-6 | 9.7 | | 57.18 | |
| III-7 | 57.8 | | 63.58 | |
| III-8 | 73.9 | | 17.1 | |
| III-9 | 8.9 | | 34.59 | |
| III-11 | 63.6 | | 35.6 | |
| III-12 | 73.6 | | 12.05 | |
| III-13 | 24.2 | | 42.9 | |
| III-14 | 23.1 | | 44.81 | |
| III-15 | 49.9 | | 37.54 | |
| III-16 | 45.6 | | 2.57 | |
| VII-1 | 12.1 | | 40.3 | |
| VII-2 | 41.9 | | 24.31 | |
| VII-3 | 27.2 | | 76.67 | |
| VII-4 | 89.2 | | 10.85 | |
| VII-5 | 6.7 | | 50.06 | |
| VII-6 | 9.4 | | 19.28 | |
| VII-7 | 18.5 | | 13.06 | |
| III-17 | 42.5 | | 86.46 | 88.10 (1 mg) |
| | | | | 80.91 (0.3 mg) |
| | | | | 96.25 (0.1 mg) |
| III-18 | 45.2 | | 84.19 | 62.6 (1 mg) |
| III-19 | 20.3 | | 88.46 | |
| III-20 | 18.5 | | 89.24 | |
| III-23 | 62.0 | | 95.5 | 95.03 (1 mg) |
| | | | | 83.97 (0.3 mg) |
| | | | | 48.46 (0.1 mg) |
| III-24 | 101.7 | | 73.8 | 95.65 (1 mg) |
| III-25 | 29.4 | | 68.59 | |
| III-27 | 70.9 | | 65.83 | |
| IV-1 | 95.9 | 65.9 (3 mg) | 80.08 | 26.41 (1 mg) |
| Control | 77.3 | 35.8 (3 mg) | 40.75 | 73.1 (30 mg) |

Control: Oxatomide

Test Example 3 (Acute toxity)

Male IcR mice (SPF) (Nippon SLC, weight:24–32 g) of 4 weeks age were fasted for 5 hours before the test. The test compound (III-2) was administered in the form of a suspension in 0.5% carboxymethylcellulose sodium salt (0.2 ml per 10 g). Survived and dead animals were autopsied at day 14 and immediately after the death, respectively. The results showed that $LD_{50}$ for p.o. and $LD_{50}$ for i.p. were >3 g/kg and >1 g/kg, respectively, both indicating low toxity.

Test Example 4 (Inhibition of experimental asthma in guinea pigs)

Male Hartley guinea pigs (N=10) were passively sensitized by intravenous injection of guinea pig antiovalbumin antiserum (titer for 3 hours PCA: 16000 times) diluted 5 times with physiological saline at a rate of 0.2 ml/animal. After 24 hours, the animal was fixed at dorsal position under urethane anesthetization and connected with a respirator (Harvard Model 683, respiratory volume: 4–6 ml/respiration; respiratory rate: 40/minute) via an incised tracheal cannula. Then 1 mg/kg Gallamine triethiodide was intravenously administered to stop the spontaneous respiration. Anaphylactic airway contraction was elicited by intravenous administration ovalbumin in a manner similar to that in Test Example 2 and animals were observed for 15 minutes. Oxatomide was administered two hours before the challenge by antigen and the test drug (compound III-2) and Ketotifen were administered orally 1 hour before the challenge. At the end of the measurement, the cannula was completely blocked and the measured values were expressed in percent of the blockage taken as the maximum contraction (100%).

TABLE 2

| compound: III-2 (1 mg/kg, p.o.) | |
| --- | --- |
| Drugs and number of animals | Inhibition % of experimental asthema in guinea pig (p.o.) |
| III-2 1 mg/kg n = 10 | 70.3*** |
| Oxatomide 1 mg/kg. n = 11 | 43.7* |
| Ketotifen 1 mg/kg n = 9 | 50.4* |

*, ***: Significance vs. control, p < 0.05, 0.001

Test Example 5 (Blood thromboxane $(TX)A_2$)

Male Wistar rats of 7 weeks old and weighing about 280 g were passively sensitized with rat anti-ovalbumin antiserum prepared according to the method of Tada and Okumura. Similarly, Hartley guinea pigs of 8 weeks old and weighing about 500 g were passively sensitized with guinea pig anti-ovalbumin antiserum prepared by immunizing with a mixed emulsion of ovalbumin and complete Freund's adjuvant (4.5:5.5) .

After 24 hours, trachea was incised under urethane ansthetiziation and cannulated with a respirator. Ovalbumin was intravenously administered to elicit the reaction while observing airway resistance according to a modified Konzett and Roessler method. Drugs were orally administered before 1 hour of elicitation of reaction. Blood samples were drawn from artery of rats and guinea pigs before the elicitaiton and after 8 minutes and 15 minutes, respectively, of the elicitation. The obtained blood samples were immediately mixed with 10 mM EDTA disodium and 0.4 mM indomethacin and centrifuged to separate blood plasma. $TXB_2$, a metabolite of $TXA_2$, in the blood plasma was partially purified by C18 column and determined by Enzyme Immunoassay Kit.

The results are shown in Table 3. In the rats, blood $TXA_2$ increased significantly after reaction and test drug (compound III-2) significantly inhibited the increase of $TXA_2$. The rate of inhibition was 68.7%. Also, in guinea pigs, blood $TXA_2$ increased after the reaction and the test drug inhibited the increase at 94.4% which was statistically significant. These results suggest that the compound III-2 inhibits production of TXA$_2$.

TABLE 3

| Animals | Drug and number of animal | Blood TXA$_2$ (ng/ml) | | Inhibition (%) |
| --- | --- | --- | --- | --- |
| | | Before reaction | After reaction | |
| Rats | Control n = 14 | 0.36 ± 0.06 | 0.93 ± 0.10### | — |
| | III-2 1 mg/kg n = 11 | 0.27 ± 0.02 | 0.45 ± 0.04*** | 68.7 |
| Guinea pigs | Control n = 5 | 0.47 ± 0.10 | 0.83 ± 0.22 | — |
| | III-2 3 mg/kg n = 5 | 0.26 ± 0.05 | 0.28 ± 0.05* | 94.4 | p < 0.001 (Significance vs. the value before reaction)
*p < 0.05 (Significance vs. control)
***p < 0.001 (Significance vs. control)

What is claimed is:

1. (Amended) A compound of the formula:

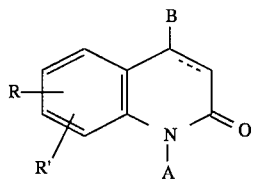

wherein the symbol of a solid line with a broken line means a single bond or a double bond;

R and R' are independently selected from the group consisting of hydrogen atom, halogen atom, lower alkyl, nitro, unsubstituted amino and substituted amino;

A and B are independently selected from the group consisting of hydrogen atom, lower alkyl optionally substituted with a lower cycloalkyl, aryl optionally substituted with one or more halogen atoms and the group: -Y-R$^2$ wherein Y is lower alkylene and R$^2$ is the group:

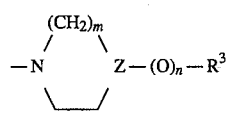

wherein m is an integer of 1 to 3, n is 0 or 1, Z is N-, >CH—, or >C=, R$^3$ is diaryl (lower) alkyl optionally substituted with one or more halogen atoms or is a condensed heterocyclic group optionally substituted with oxo, with the proviso that (a) one of A and B is the group -Y-R$^2$, and (b) when A is hydrogen atom or an unsubstituted lower alkyl group and B is the group -Y-R$^2$, then Z is >CH— or >C= if R$^3$ is a condensed heterocyclic group optionally substituted with oxo and n is O or a pharmaceutically acceptable salt thereof.

2. A compound according to claim 1 wherein A is the group:

Y-R$^2$ and B is selected from the group consisting of hydrogen atom, lower alkyl optionally substituted with a lower cycloalkyl, and aryl optionally substituted with one or more halogen atoms.

3. A compound according to claim 2 wherein Z is >CH—, n is 0 and R$^3$ is 1H-indol-3-yl.

4. A compound according to claim 1 wherein B is the group:

Y-R$^2$ and A is selected from the group consisting of hydrogen atom, lower alkyl optionally substituted with a lower cycloalkyl, and aryl optionally substituted with one or more halogen atoms.

5. A pharmaceutical composition comprising a therapeutically or prophylactically effective amount of at least one compound of claim 1 or a pharmaceutically acceptable salt thereof in association with a pharmaceutically acceptable carrier or diluent.

6. A method of treating allergic diseases which comprises administering to a subject in need of such treatment a therapeutically or prophylactically effective amount of at least one compound of the formula:

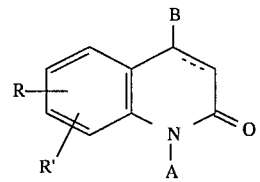

wherein the symbol of a solid line with a broken line means a Single bond or a double bond;

R and R' are independently selected from the group consisting of hydrogen atom, halogen atom, lower alkyl, nitro, unsubstituted amino and substituted amino;

A and B are independently selected from the group consisting of hydrogen atom, lower alkyl optionally substituted with a lower cycloalkyl, aryl optionally substituted with one or more halogen atoms and the group: -Y-R$^2$ wherein Y is lower alkylene and R$^2$ is the group:

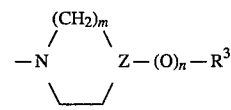

wherein m is an integer of 1 to 3, n is 0 or 1, Z is >N-, >CH—, or >C=, R$^3$ is diaryl (lower) alkyl optionally substituted with one or more halogen atoms or is a condensed heterocyclic group optionally substituted with oxo, with the proviso that (a) one of A and B is the group -Y-R$^2$, and (b) when A is hydrogen atom and B is the group -Y-R$^2$, then Z is >CH— or >C= if R$^3$ is a condensed heterocyclic group optionally substituted with oxo and n is O or pharmaceutically acceptable salt thereof.

7. A compound of the formula:

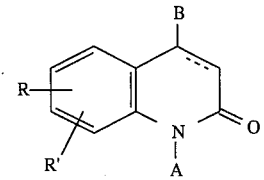

or a pharmaceutically acceptable salt thereof, wherein the symbol of a solid line with a broken line means a single bond or a double bond;

R and R' are independently selected from the group consisting of hydrogen atom, halogen atom, lower alkyl, nitro, unsubstituted amino and substituted amino;

A and B are independently selected from the group consisting of hydrogen atom, lower alkyl optionally substituted with a lower cycloalkyl, aryl optionally substituted with one or more halogen atom and the group: -Y-R² wherein Y is lower alkylene and R² is the group:

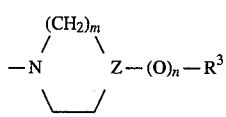

wherein m is an integer of 1 to 3, n is 0 or 1, Z is >CH— or >C=, R³ is diaryl (lower) alkyl optionally substituted with one or more halogen atoms or is a condensed heterocyclic group optionally substituted with oxo, with the proviso that at least one of A and B is the group -Y-R².

8. The compound according to claim 7 wherein B is the group: -Y-R² and A is selected from the group consisting of hydrogen atom, lower alkyl which is unsubstituted or substituted with a lower cycloalkyl, and aryl optionally substituted with one or more halogen atoms.

9. The compound according to claim 8, wherein Z is >CH—, n is 0 and R³ is 1H-indol-3-yl.

10. The compound according to claim 8, wherein Z is >C=, n is 0 and R³ is 4,9-dihydro-10H-benzocyclohepta[1.2b]thiophen-10-one.

11. The compound according to claim 8 wherein Z is >CH—, n is 1 and R³ is diphenylmethyl.

12. A compound of the formula:

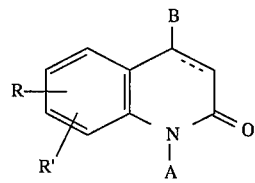

wherein the symbol of a solid line with a broken line means a single bond or a double bond;

R and R' are independently selected from the group consisting of hydrogen atom, halogen atom, lower alkyl, nitro, unsubstituted amino and substituted amino;

A and B are independently selected from the group consisting of hydrogen atom, lower alkyl optionally substituted with a lower cycloalkyl, aryl optionally substituted with one or more halogen atoms and -Y-R², wherein Y is lower alkylene and R² is the group:

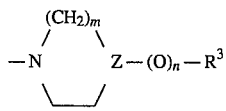

wherein m is an integer of 1 to 3, n is 0 or 1, Z is >N-, R³ is diaryl (lower) alkyl optionally substituted with one or more halogen atoms with the proviso that at least one of A and B is the group -Y-R².

13. The compound according to claim 12 wherein B is the group: -Y-R² and A is selected from the group consisting of hydrogen atom, lower alkyl optionally substituted with a lower cycloalkyl, and aryl optionally substituted with one or more halogen atoms.

14. The compound according to claim 13, wherein Z is >N-, n is 0 and R³ is diphenylmethyl optionally ring-substituted with halogen.

15. A compound of the formula:

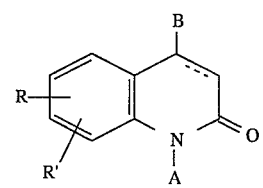

or a pharmaceutically acceptable salt thereof wherein the symbol of a solid line with a broken line means a single bond or a double bond;

R and R' are independently selected from the group consisting of hydrogen atom, halogen atom, lower alkyl, nitro, unsubstituted amino and substituted amino;

A and B are independently selected from the group consisting of hydrogen atom, lower alkyl optionally substituted with a lower cycloalkyl, aryl optionally substituted with one or more halogen atoms and the group -Y-R² wherein Y is lower alkylene and R² is the group:

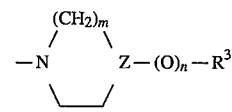

wherein m is an integer of 1 to 3, n is 1, Z is >N-, R³ is diaryl(lower)alkyl optionally substituted with one or more halogen atoms or is a condensed heterocyclic group optionally substituted with oxo, with the proviso that one of A and B is the group -Y-R².

16. A compound of the formula:

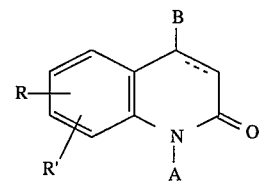

or a pharmaceutically acceptable salt thereof wherein the symbol of a solid line with a broken line means a single bond or a double bond;

R and R' are independently selected from the group consisting of hydrogen atom, halogen atom, lower alkyl, nitro, unsubstituted amino and substituted amino;

A is selected from the group consisting of lower alkyl optionally substituted with a lower cycloalkyl, aryl optionally substituted with one or more halogen atoms and the group -Y-R²;

B is A, hydrogen or the group -Y-R²;

wherein Y is lower alkylene and R² is the group:

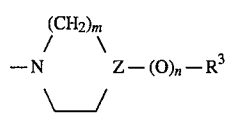

wherein m is an integer of 1 to 3, n is 0 or 1, Z is >N-, $R^3$ is diaryl(lower)alkyl optionally substituted with one or more halogen atoms or is a condensed heterocyclic optionally substituted with oxo, said heterocyclic being indole, benzofuran, benzothiophene, indazole, quinoline, chromene, cinnoline, benzozepine, benzodiazepine, carbazole, phenoxazine, phenothiazine, dibenzoazepine, benzocycloheptathiophene, indolidine, purine, quinolidine, naphtylidine or carboline or the partially or completely hydrogenated counterparts thereof, with the proviso that at least one of A and B is the group $-Y-R^2$.

17. A pharmaceutical composition comprising a therapeutically or prophylactically effective amount of claim 7 or a pharmaceutically acceptable salt thereof.

18. A pharmaceutical composition comprising a therapeutically or prophylactically effective amount of a compound of claim 12 or a pharmaceutically acceptable salt thereof.

19. A pharmaceutical composition comprising a therapeutically or prophylactically effective amount of a compound of claim 15 or a pharmaceutically acceptable salt thereof.

20. A pharmaceutical composition comprising a therapeutically or prophylactically effective amount of a compound of claim 16 or a pharmaceutically acceptable salt thereof.

* * * * *

UNITED STATES PATENT AND TRADEMARK OFFICE
CERTIFICATE OF CORRECTION

PATENT NO. : 5,457,099

DATED : October 10, 1995

INVENTOR(S) : Takeshi Shogaki, et al.

It is certified that error appears in the above-identified patent and that said Letters Patent is hereby corrected as shown below:

Column 23, line 17: "-piperidinyl" should read --1-piperidinyl--

Column 27, under "State", lines 2 & 6: "white crystals" should read --white needles--

Column 28, last line: "$C_{23}H_{23}N_3O(357.45)8\ (M+H)$" should read --$C_{23}H_{23}N_3O(357.43)\ 358\ (M+H)$--

Column 29, line 8: "(413.49)4" should read --(413.49) 414--

Column 29, line 9: "(409.43)0(M+H)" should read --(409.53) 410 (M+H)--

UNITED STATES PATENT AND TRADEMARK OFFICE
CERTIFICATE OF CORRECTION

PATENT NO. : 5,457,099

DATED : October 10, 1995

INVENTOR(S) : Takeshi Shogaki, et al.

It is certified that error appears in the above-identified patent and that said Letters Patent is hereby corrected as shown below:

Column 30, line 12: "$C_{28}H_{28}ClN_3O(457588M+H)$" should read --$C_{28}H_{28}ClN_3O\,(457.98)\,458\,(M+H)$--

Column 30, line 13: "$C_{28}H_{28}N_2O_2(424\cdot H_{54}\,425(M+H)$" should read --$C_{28}H_{28}N_2O_2\,(424.54)\,425\,(M+H)$--

Column 31, line 1: "454587(M+H)" should read --(452.57) 453 (M+H)--

Column 31, line 4: "(371.49)2(M+H)" should read --(371.49) 372 (M+H)--

Column 32, line 6: "450507(M+H)" should read --(450.37) 450 (M+H)--

Column 32, line 9: "$O_2(428.53\,\,429(M+H)$" should read --$O_2\,(428.53)\,429\,(M+H)$--

UNITED STATES PATENT AND TRADEMARK OFFICE
CERTIFICATE OF CORRECTION

PATENT NO. : 5,457,099
DATED : October 10, 1995
INVENTOR(S) : Takeshi Shogaki, et al.

It is certified that error appears in the above-identified patent and that said Letters Patent is hereby corrected as shown below:

Column 32, line 10: "$O_4(514.62$ $515(M+H)$" should read --$O_4$ (514.62) 515 (M+H)--

Column 33, line 3: "(385.58)6(M+H)" should read --(385.51) 386 (M+H)--

Column 34, line 8: "(413.56)4(M+H)" should read --(413.56) 414 (M+H)--

Column 35, line 2: "(373.48)374(M+H)" should read --(373.48) 374 (M+H)--

Column 36, line 12: "360-1)" should read --36-1)--

Column 37, line 1: "(419.952,0(M+H)" should read --(419.95) 420 (M+H)--

Column 37, line 7: "$4\text{-}CH_3$ $CH_6$ $H_4$" should read --$4\text{-}CH_3$ $C_6H_4$-- and "$ClN_3O$" should read --$N_3O$--

UNITED STATES PATENT AND TRADEMARK OFFICE
CERTIFICATE OF CORRECTION

PATENT NO. : 5,457,099
DATED : October 10, 1995
INVENTOR(S) : Takeshi Shogaki, et al.

It is certified that error appears in the above-identified patent and that said Letters Patent is hereby corrected as shown below:

Column 42, line 12: "3,71" should read --3.71--

Column 42, line 13: "3,82" should read --3.82--

Column 44, line 5: "6.97-7.53" should read --6.97 ~ 7.53--

Column 44, line 12: "6.85-7.57" should read --6.85 ~ 7.57--

Column 46, line 4: "3,30" should read --3.30--

Column 48, line 22: "NHCO" should read --N$\underline{H}$CO--

Column 48, line 39: "NHCO" should read --N$\underline{H}$CO--

Column 50, line 1: "1,50" should read --1.50--

Column 50, line 16: "7,90" should read --7.90--

Column 50, line 18: "3,72" should read --3.72--

UNITED STATES PATENT AND TRADEMARK OFFICE
CERTIFICATE OF CORRECTION

PATENT NO. : 5,457,099

DATED : October 10, 1995

INVENTOR(S) : Takeshi Shogaki, et al.

It is certified that error appears in the above-identified patent and that said Letters Patent is hereby corrected as shown below:

Column 51, line 46, insert the following:

--No.   Formula   IR($\nu$ max, cm$^{KBr}$)   H-NMR($\delta$ ,CDCl , 90MHz)

Column 53, line 22: "32751640" should read
--3275
 1640--

Column 54, lines 1-5: " 3.10-3.60(m, 3H, CH$_2$CH$_2$Br, 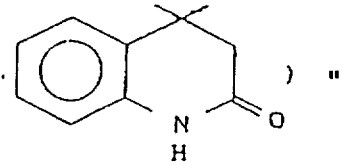 ) "

should read -- 3.10~3.60(m, 3H, CH$_2$CH$_2$Br, 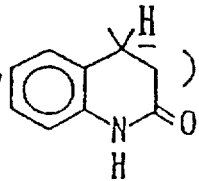 ) --

UNITED STATES PATENT AND TRADEMARK OFFICE
CERTIFICATE OF CORRECTION

PATENT NO. : 5,457,099

DATED : October 10, 1995

INVENTOR(S) : Takeshi Shogaki, et al.

Page 6 of 7

It is certified that error appears in the above-identified patent and that said Letters Patent is hereby corrected as shown below:

Column 67, before line 1, insert the following:
--No.  IR($\nu_{max}^{KBr}$, cm$^{-1}$)    H-NMR($\delta$, CDC$\ell_3$, 90MHz)--

Column 67, line 12: "7.35" should read --3.75--

Column 67, line 22: "N$\underline{H}$CO" should read --N$\underline{H}$CO--

Column 69, line 13: "1.26(s," should read --1.26(d,--

Column 71, line 16: "CH$_2$ )" should read --CH$_2$ -,--

Column 71, line 37: "1.86 $\sim$ 3.10" should read --1.86-3.10--

Column 77, line 21: delete "(Amended)"

Column 77, line 50, Claim 1: "is N-" should read -- is$>$ N- --

Column 77, line 64, Claim 2: "Y-R$^2$" should read -- -Y-R$^2$ --

Column 78, line 5, Claim 4: "Y-R$^2$" should read -- -Y-R$^2$ --

UNITED STATES PATENT AND TRADEMARK OFFICE
CERTIFICATE OF CORRECTION

PATENT NO. : 5,457,099
DATED : October 10, 1995
INVENTOR(S) : Takeshi Shogaki, et al.

It is certified that error appears in the above-identified patent and that said Letters Patent is hereby corrected as shown below:

Column 79, line 23, Claim 7: delete "at least"

Column 79, line 33, Claim 10: after "benzo" insert --[4.5]--

Column 79, line 67, Claim 12: delete "at least"

Column 81, lines 10 & 11, Claim 16: after "heterocyclic" insert --group--

Column 81, line 13 Claim 16: "benzozepine" should read --benzazepine--

Column 81, line 15, claim 16: "dibenzoazepine" should read --dibenzazepine--

Column 82, lines 1-2, Claim 16: delete "at least"

Column 82, line 4, Claim 17: after "amount" insert --of a compound--

Signed and Sealed this

Thirty-first Day of August, 1999

Attest:

*Attesting Officer*

Q. TODD DICKINSON

*Acting Commissioner of Patents and Trademarks*